(12) United States Patent
Daniels

(10) Patent No.: US 11,382,155 B2
(45) Date of Patent: Jul. 5, 2022

(54) SYSTEM AND METHOD FOR OUT-OF-BAND PAIRING OF STERILE DEVICE WITH NON-STERILE DEVICE

(71) Applicant: Canon U.S.A., Inc., Melville, NY (US)

(72) Inventor: Barret Daniels, Cambridge, MA (US)

(73) Assignee: Canon U.S.A., Inc., Melville, NY (US)

( * ) Notice: Subject to any disclaimer, the term of this patent is extended or adjusted under 35 U.S.C. 154(b) by 94 days.

(21) Appl. No.: 17/023,063

(22) Filed: Sep. 16, 2020

(65) Prior Publication Data
US 2021/0084700 A1  Mar. 18, 2021

Related U.S. Application Data

(60) Provisional application No. 62/902,031, filed on Sep. 18, 2019.

(51) Int. Cl.
*H04B 7/00* (2006.01)
*H04W 76/14* (2018.01)
(Continued)

(52) U.S. Cl.
CPC ............ *H04W 76/14* (2018.02); *G16H 40/20* (2018.01); *H04L 9/3226* (2013.01); *H04W 4/80* (2018.02);
(Continued)

(58) Field of Classification Search
CPC ..... H04W 76/14; H04W 4/80; H04W 12/037; H04W 12/50; G16H 40/20; H04L 9/3226
(Continued)

(56) References Cited

U.S. PATENT DOCUMENTS 6,733,473 B1 * 5/2004 Reifart ................ A61M 25/104
604/96.01
8,568,467 B2 * 10/2013 Dorn ........................ A61F 2/95
623/1.12
(Continued)

FOREIGN PATENT DOCUMENTS

KR    10-2018-0038868 A    4/2018

OTHER PUBLICATIONS

Freudenthal, E. et al., "Suitability of NFC for Medical Device Communication and Power Delivery", Dec. 2007.
(Continued)

*Primary Examiner* — April G Gonzales
(74) *Attorney, Agent, or Firm* — Canon U.S.A., Inc., IP Division

(57) ABSTRACT

System and methods for out-of-band pairing sterile medical device with non-sterile devices without compromising sterility thereof. A system includes a sterile medical device; a non-sterile computing device; at least one near field communication (NFC) tag; and a sterile packaging enclosing the sterile medical device. In one example, a sterile percutaneous needle guidance device needs to pair and communicate with a non-sterile computer. The sterile device has an NFC tag embedded in the sterile device and an NFC tag embedded in the sterile packaging. The two NFC tags include identification information duplicate of each other. Before opening the sterile packaging either NFC tag can be scanned with the non-sterile device to initiate wireless pairing. If the sterile package is opened before pairing, the NFC tag contained in the packaging can be brought out of the sterile field and scanned with the non-sterile computer thus preserving the sterility of the sterile device.

20 Claims, 13 Drawing Sheets

(51) Int. Cl.
  *H04W 4/80* (2018.01)
  *H04L 9/32* (2006.01)
  *G16H 40/20* (2018.01)
  *H04W 12/037* (2021.01)
  *H04W 12/50* (2021.01)

(52) U.S. Cl.
  CPC ......... *H04W 12/037* (2021.01); *H04W 12/50* (2021.01)

(58) Field of Classification Search
  USPC .......................................... 455/41.1
  See application file for complete search history.

(56) References Cited

U.S. PATENT DOCUMENTS

| | | | | |
|---|---|---|---|---|
| 9,622,706 | B2* | 4/2017 | Dick | A61B 5/0062 |
| 9,800,663 | B2* | 10/2017 | Arrizza | H04B 5/02 |
| 10,449,339 | B2* | 10/2019 | Wilson | A61M 25/0028 |
| 10,485,952 | B2* | 11/2019 | Garrison | A61M 25/0108 |
| 2011/0022411 | A1* | 1/2011 | Hjelm | G16H 40/67 |
| | | | | 705/2 |
| 2011/0238041 | A1* | 9/2011 | Lim | A61M 25/0054 |
| | | | | 604/525 |
| 2014/0273824 | A1* | 9/2014 | Fenner | A61B 5/0031 |
| | | | | 455/41.1 |
| 2015/0023204 | A1* | 1/2015 | Wik | H02J 50/10 |
| | | | | 370/254 |
| 2015/0137992 | A1* | 5/2015 | Potyrailo | G08B 21/18 |
| | | | | 340/870.07 |
| 2015/0207796 | A1* | 7/2015 | Love | A61B 5/002 |
| | | | | 726/4 |
| 2017/0091498 | A1* | 3/2017 | Forster | G06K 7/10297 |
| 2018/0193042 | A1* | 7/2018 | Wilson | A61B 17/12109 |
| 2019/0201122 | A1* | 7/2019 | Shelton, IV | A61B 34/76 |

OTHER PUBLICATIONS

Bix, L., et al., "Medical Device Packaging", Jan. 2009, pp. 713-727.
Marques, G, et al., "Internet of Things Architectures, Technologies, Applications, Challenges, and Future Directions for Enhanced Living Environments and Healthcare Systems: A Review", Electronics, Sep. 24, 2019, pp. 1-27. vol. 8.
Potgantwar, A. D., et al., "A Standalone RFID and NFC based Healthcare System", iJIM, Apr. 2013, pp. 73-79, vol. 7, No. 2.
Bluetooth Special Interest Group, Bluetooth® Secure Simple Pairing Using NFC, Application Document, NFC ForumTM, NFCForum-AD-BTSSP_1_1, Jan. 9, 2014.
Fomichev, M., et al., "Survey and Systematization of Secure Device Pairing", pp. 1-34.

* cited by examiner

FIG. 5

S501
DURING MANUFACTURE, ASSEMBLY, OR FIRST USE: GENERATE IDENTIFICATION INFORMATION AND WRITE IT INTO BOTH NFC TAG1 OF STERILE DEVICE AND NFC TAG2 OF STERILE PACKAGING

S502
DURING MEDICAL PROCEDURE BEFORE NFC PAIRING: USER MAY SEPARATE STERILE DEVICE FROM ITS PACKAGING (PACKAGE OPENED)

S503
DURING NFC PAIRING: SCAN NFC TAG 2 OF STERILE PACKAGING WITH NFC TRANSCEIVER OF NON-STERILE DEVICE, WHILE STERILE DEVICE REMAINS IN STERILE FIELD

S504
NON-STERILE DEVICE READS IDENTIFYING INFORMATION FROM NFC TAG2 OF STERILE PACKAGING

S506
STERILE DEVICE REMAINS IN STERILE FILED AND IS TURNED ON

S508
STERILE DEVICE READS INFORMATION FROM ITS NFC TAG1 AND SEARCHES FOR HOST (NON-STERILE DEVICE)

S509
STERILE DEVICE AND NON-STERILE DEVICE ESTABLISH SECURE WIRELESS CONNECTION WITOUT LOSING STERILITY OF STERILE DEVICE

SYSTEM AND METHOD FOR OUT-OF-BAND PAIRING OF STERILE DEVICE WITH NON-STERILE DEVICE

CROSS-REFERENCE TO RELATED APPLICATIONS

The present application claims priority to U.S. provisional application 62/902,031, filed Sep. 18, 2019, the disclosure of which is incorporated by reference herein in its entirety.

BACKGROUND INFORMATION

Field of Disclosure

The present disclosure relates to medical devices. More particularly, the disclosure exemplifies a system and method for out-of-band pairing of a sterile device with a non-sterile device in a medical environment such as, for example, an operating room.

Description of Related Art

Sterilization refers to any process that effectively renders any surface, equipment or article free from viable microorganisms. Sterility and its maintenance, together with the prevention of cross-infection, are at the top of any list of critical factors in patient care. In practice, Sterility Assurance Level (SAL) is used as a measure of the survival level of microorganisms after terminal sterilization. Items such as medical devices can only be categorized as "sterile" if the chance of an item remaining contaminated after sterilization is less than or equal to one chance in a million. Therefore, the packaging around medical devices is carefully designed so that it allows those devices to be sterilized, provides a microbial barrier and maintains sterility effectively up to the point of use. This type of packaging creates a sterile barrier system (SBS) and is an essential part of a sterile medical device.

Single use sterile medical devices are prevalent in the medical device industry. Sterile medical devices are usually delivered to a medical facility (e.g., hospital) in terminally sterile packaging and are used once for a single patient and discarded following the procedure. Single use sterile devices are often preferred over reusable devices due to the decreased risk of improper cleaning, disinfecting, and lower chance of infection or cross contamination. In the past, in order to be disposable, sterile medical devices were typically made from low-grade injection molded plastics and most single-use sterile devices did not include electronic components.

Recently, the internet of things (IoT) industry has revolutionized the consumer electronics market with the advent of wirelessly connected devices. With the rapid growth of the IoT industry and the low cost of electronic components, several medical device manufacturers now produce single use disposable medical devices which include highly advanced electronic components that must interact with non-disposable medical equipment. To that end, many wireless communication protocols, including wireless fidelity (WiFi), Bluetooth, Z-Wave, ZigBee, near field communication (NFC), radio frequency identification (RFID), IPv6 over low-power wireless area networks (6LoWPAN), etc., have been developed to facilitate the proliferation of medical devices capable of wirelessly connecting to each other.

Near field communication (NFC) is a type of short-range radio frequency communication technology, operating at about 13.56 MHz and in a bandwidth of about 2 MHz, which allows for read-only and read-write communications between a NFC-enabled RF device reader and a NFC-enabled device. NFC operation is based on inductive coupling between two loop antennas, which allows for sharing of power and data between NFC-enabled devices at a short distance. Typically, for proper operation, the distance between a NFC-enabled reader and a NFC-enabled device needs to be about under about 10 centimeters (cm) and more preferably about 5 cm or two inches.

Security is of paramount importance in wirelessly connected medical devices and thus wireless encryption is a necessity. Also, for devices requiring an unsterile and sterile component to interface with each other, medical device packaging is an important aspect to minimize the chance of loss of sterility. However, the pairing process of a sterile medical device to a non-sterile medical device is prone to accidental loss of sterility when a sterile component comes into contact with an unsterile user or unsterile component.

Many device manufacturers use near field communication (NFC) or radio-frequency identification (RFID) technologies to exchange device identifying information such as a wireless identifier and an encryption key out-of-band between devices in order to encrypt communications securely. This process is referred to as out-of-band (OOB) paring. OOB pairing is a secure way of sharing a wireless identifier and/or encryption key without using the main communication channel or protocol. In the case of Bluetooth enabled devices, for example, OOB paring could use a protocol other than Bluetooth; for example, pairing could use a different 2.4 GHz protocol, such as direct WiFi or ZigBee or 6LoWPAN, etc., or it could use a different communication frequency, such as NFC. Bluetooth OOB paring using NFC is well known. See, for example, Application Document "Bluetooth® Secure Simple Pairing Using NFC" published by NFC Forum, Inc., 2014. As explained above, OOB pairing using NFC and RFID technology requires devices to be in close proximity to each other or to even touch each other. This pairing process of a sterile medical device to a non-sterile medical device is prone to accidental loss of sterility when a sterile component comes into contact with an unsterile user or unsterile component. However, the issue of maintaining appropriate sterility during the paring process has not been addressed by the consumer electronic industry.

For example, U.S. Pat. No. 9,800,663, "Associating Dialysis Accessories Using Near Field Communications", describes pairing a Dialysis machine with Dialysis accessories such as a blood pressure cuff using NFC technology to exchange a wireless identifier unique to the dialysis machine accessory device. The dialysis machine then uses the wireless identifier to establish a wireless communication with the accessory granting permissions to the dialysis accessory to control functions of the dialysis machine. Similarly, patent application publication US 2014/0273824, "Systems, Apparatus and Methods Facilitating Secure Pairing of an Implantable Device with a Remote Device Using Near Field Communication", describes exchanging information with an implantable device using NFC protocols. In this case, an implantable medical device contains a NFC component externally attached to the implant. The NFC component is configured to transmit identification information associated with the implantable device to a reader using the NFC protocol. Exchange of this information allows for pairing of the implant with an external remote device over a secondary communication protocol other than NFC, such as Bluetooth. Also, patent application publication US 2017/0091498 discloses using RFID devices integrated or included in the packaging of medical devices to facilitate a secure and authorized pairing with a host system. In publication US 2017/0091498, the medical device is a wearable sensor, a sensing patch attachable to a patient, or a sensing patch used in cooperation with medication administration to a patient. Therefore, although the RFID may ensure secure pairing of the medical device, sterility of the medical device is not maintained when the medical device is applied to the patient.

In U.S. Pat. No. 9,800,663, none of the dialysis accessories are sterile and thus this patent does not address the need of pairing a sterile device to a non-sterile device without compromising sterility. Similarly, publication US 2014/0273824 is limited to implantable medical devices only, and it covers exchanging information over NFC only after the implant is implanted into the patient. Therefore, the need of pairing a sterile medical device with a non-sterile medical device without compromising sterility remains.

Indeed, the main barrier for adoption of these wireless technologies in sterile medical devices is the challenge of secure wireless pairing of a sterile medical device with another non-sterile and non-disposable device such as a computer without compromising the sterility of the sterile disposable device. Physical interaction between a sterile medical device and a non-sterile medical device will inevitably render the sterile device non-sterile. This challenge is unique to the application of these wireless technologies to medical devices and thus has not been addressed by the consumer electronic industry.

SUMMARY OF EXEMPLARY EMBODIMENTS

According to at least one embodiment of the present disclosure, there is provided a system and method for out-of-band pairing a sterile medical device with a non-sterile computing device without compromising sterility of the sterile medical device.

The system includes a sterile medical device; a non-sterile computing device; at least one NFC (near field communication) tag; and a sterile packaging enclosing the sterile medical device. In one example, a sterile percutaneous needle guidance device needs to pair and communicate with a non-sterile computer. The sterile guidance device has a first NFC tag embedded in the device and a second NFC tag embedded in the sterile packaging. The two NFC tags are duplicate of each other. Before opening the sterile packaging either NFC tag can be scanned with the non-sterile device to initiate wireless pairing. If the sterling packaging is opened before pairing, then the second NFC tag contained in the packaging can be brought out of the sterile field and scanned with the non-sterile computing device thus preserving the sterility of the percutaneous needle guidance device.

These and other objects, features, and advantages of the present disclosure will become apparent upon reading the following detailed description of exemplary embodiments of the present disclosure, when taken in conjunction with the appended drawings, and provided claims.

BRIEF DESCRIPTION OF DRAWINGS

Further objects, features and advantages of the present disclosure will become apparent from the following detailed description when taken in conjunction with the accompanying figures showing illustrative embodiments of the present disclosure.

FIG. 5 is a flowchart of an exemplary process for paring a sterile medical device with a non-sterile computing device wherein, during manufacturing, identification information is written into a NFC tag of the sterile device and into a NFC tag of the sterile packaging.

DETAILED DESCRIPTION OF EXEMPLARY EMBODIMENTS

Figure 1:
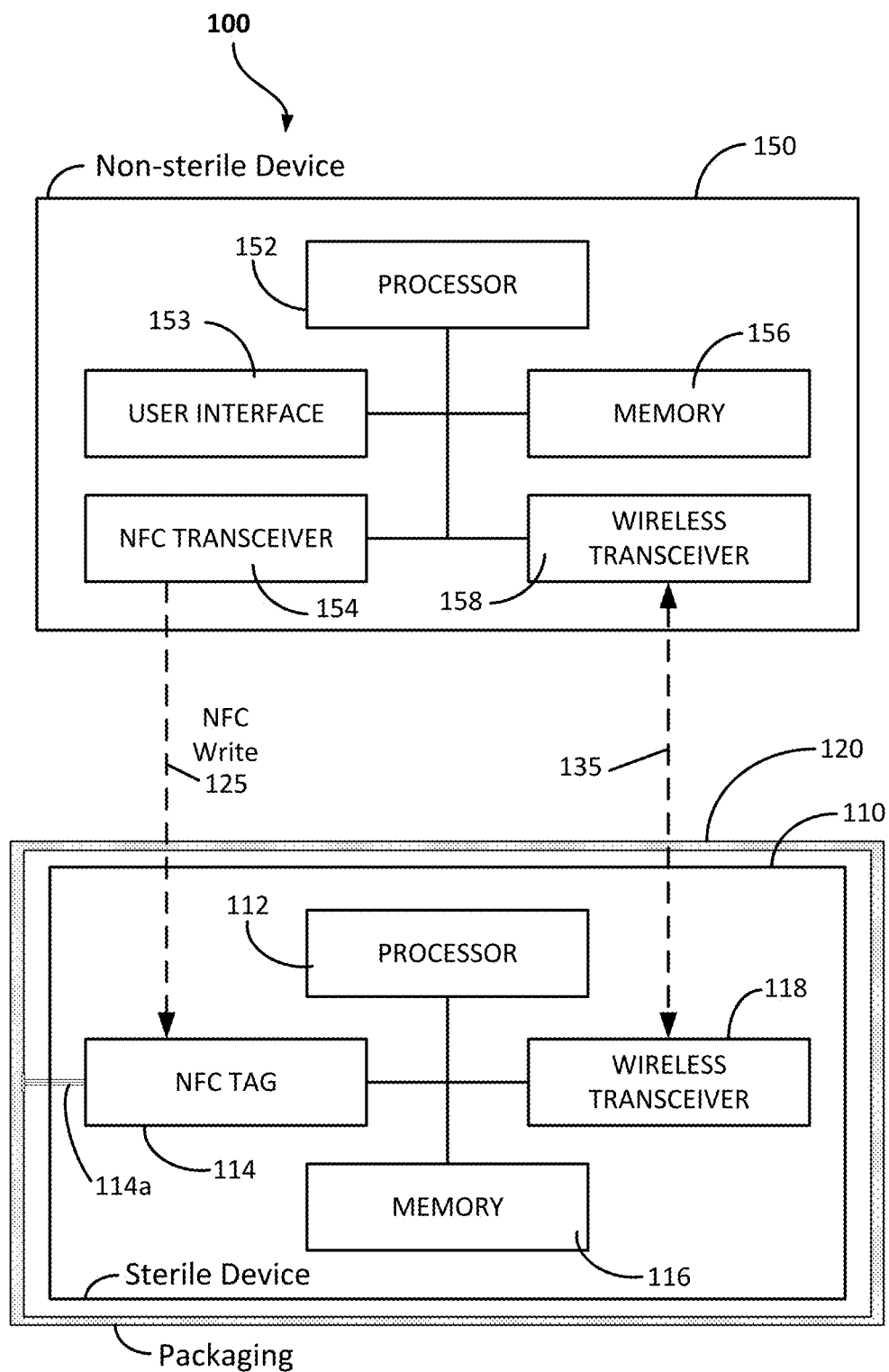
FIG. 1 is a diagram of an exemplary system for paring a sterile medical device with a non-sterile computing device using short-range near field communication protocols.

The embodiments are based on the object of providing a system and method for out-of-band pairing a sterile medical device with a non-sterile computing device without compromising sterility of the sterile medical device.

In referring to the description, specific details are set forth in order to provide a thorough understanding of the examples disclosed. In other instances, well-known methods, procedures, components and circuits have not been described in detail as not to unnecessarily lengthen the present disclosure. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed. As used herein, the term "sterile" refers to its common medical definition meaning totally clean and substantially free from bacteria or other living microorganisms. Similarly the terms unsterile and non-sterile are interchangeably used to mean not free of living organisms and microorganisms, as in an unsterile medical instrument or a medical operation done in a non-sterile environment.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached", "coupled" or the like to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown in one embodiment can apply to other embodiments. It will also be appreciated by those of skill in the art that references to a structure or feature that is disposed "adjacent" to another feature may have portions that overlap or underlie the adjacent feature. When used, term "and/or", may be abbreviated as "/", and it includes any and all combinations of one or more of the associated listed items, if so provided.

Spatially relative terms, such as "under" "beneath", "below", "lower", "above", "upper", "proximal", "distal", and the like, may be used herein for ease of description to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly. Similarly, the relative spatial terms "proximal" and "distal" may also be interchangeable, where applicable.

The term "about" or "approximately" as used herein means, for example, within 10%, within 5%, or less. In some embodiments, the term "about" may mean within measurement error. In this regard, where described or claimed, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range, if recited herein, is intended to include all sub-ranges subsumed therein.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. As used herein, the singular forms "a", "an", "said" and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated. It is further noted that some claims may be drafted to exclude any optional element; such claims may use exclusive terminology as "solely," "only" and the like in connection with the recitation of claim elements, or it may use of a "negative" limitation.

The word "exemplary" is used herein to mean "serving as an example, instance, or illustration." Any aspect described herein as "exemplary", unless specifically stated, is not necessarily to be construed as preferred or advantageous over other aspects.

The term "processor" can refer to substantially any logic and/or software-based computing processing unit or device. The term "memory" can refer to volatile memory or non-volatile memory, or it can include both volatile and non-volatile memory. The memory (e.g., data storage) of the embodiments includes any suitable type of information storage component relevant to operation and functionality of a processor.

Near field communication (NFC) is a set of standards for mobile devices, such as smart phones, contactless cards, and similar devices to establish radio communication with each other by touching them together or bringing them into close proximity, usually no more than a few centimeters. NFC devices communicate via magnetic field induction, where two loop antennas are located within each other's near field, effectively forming an air-core transformer. Communication is also possible between an NFC device and an unpowered NFC chip; an unpowered NFC chip is called a "NFC tag" or simply "tag". NFC involves an initiator and a target; NFC devices take very simple form factors such as tags, stickers, key fobs, or cards that do not require batteries. NFC peer-to-peer communication is possible, provided that both devices are powered. As the names imply, the initiator is the device that initiates communication; it also controls the data exchanges. The target device is passive device that responds to the request from the initiator and accepts the communication with the initiator to happen. The initiator actively generates an RF field that can power the passive target. Radio Frequency Identification (RFID) uses essentially the same working standards as NFC. However, NFC has an essential extension over RFID which is the communication mode between two active devices. Thus, in the present disclosure, the term "NFC tag" also includes the term "RFID tag", and/or any other passive tag that communicates via magnetic field induction. An NFC initiator can be, for example, an RFID reader or a smartphone. In proximity of another NFC device, the NFC initiator initiates communication then collects information from the target (tag) or runs an action according to the collected information. For example, obtaining identification of a commercial article bearing an NFC tag is a basic example of collecting information. Pairing of a Bluetooth® music player (an NFC initiator) with an active Bluetooth® speaker (an NFC target) is a good example of an action resulting from an NFC transaction.

The term "pairing" refers to a process used in the field of computer networking for establishing an initial link or connection between two computing devices to enable communication between them. For example, Bluetooth pairing is necessary whenever two Bluetooth devices connect to each other to share resources. An example is the use of Bluetooth communication protocol to pair two devices like a set of headphones and a mobile phone or laptop. A Bluetooth pairing process is typically triggered automatically the first time a device receives a connection request from a device with which it is not yet paired. In order for Bluetooth pairing to occur, a minimum of security information has to be exchanged between the two devices. This security information, such as "password" or "passkey" is a code shared by both Bluetooth devices; the passkey is used to ensure that both devices/users have agreed to pair with each other. Out of band (OOB) pairing is a paring process designed for scenarios where an out of band communication technique is used to discover the paring devices as well as to exchange or transfer security information which would be used in the pairing process.

Currently, some Bluetooth enabled devices, such as smartphones and tablets use NFC to 'tap to pair' between devices, and use standard Bluetooth protocol for normal communication. Since NFC has very short-range communication (about 2 inches or less), the close proximity between NFC-enabled devices serves as an assurance that the two devices are indeed meant to be paired together. Therefore, NFC is a good communications interface for OOB pairing. As an example, for a user who has a smartphone and Bluetooth headphones, if both devices have Bluetooth and NFC capabilities, the user will initially touch the two devices together, and is given the option to pair. This is a single touch process where security information is exchanged between the two devices under NFC protocol. If the option to pair is confirmed ("YES" is selected), the pairing is successful, and communication between the smartphone and Bluetooth headphones takes place under standard Bluetooth protocol.

Throughout the figures, the same reference numerals and characters, unless otherwise stated, are used to denote like features, elements, components, functions or portions of the illustrated embodiments. Moreover, while the subject disclosure will now be described in detail with reference to specific figures, it is done so in connection with the illustrative exemplary embodiments. It is intended that changes and modifications can be made to the described exemplary embodiments without departing from the true scope and spirit of the subject disclosure as defined by the appended claims.

<FIG. 1>

FIG. 1 illustrates an exemplary diagram of a system 100 including a sterile medical device 110 and a non-sterile computing device 150. The medical system 100 shows the non-sterile computing device 150 pairing with the sterile medical device no via an NFC signal 125 (short-range signal), and shows the sterile medical device no wirelessly connecting to the non-sterile computing device 150 via a wireless connection 135 (long-range signal). In its basic form, the sterile medical device no includes a processor 112, a memory 116, a wireless transceiver 118, and an integrated or embedded (near field communication) NFC tag 114. As shown in FIG. 1, the sterile medical device no and the NFC tag 114 are enclosed in a sterile packaging 120. In at least some implementations, the NFC tag 114 may be connected to both the sterile medical device no and the sterile packaging 120 (e.g. by a temporary connection 114a). Alternatively, as discussed in further detail below, the sterile packaging 120 may preferably include its own NFC tag.

The processor 112 controls all operations of the sterile medical device 110. The processor 152 controls all operations of the non-sterile computing device iso. The processor 112/152 may also be referred to as a central processing unit (CPU). Additionally, the term processor may also refer to an integrated circuit (IC), an application specific integrated circuit (ASIC), a digital signal processor (DSP), a programmable logic controller (PLC), and the like. Memory 116, which may include both read-only memory (ROM) and random access memory (RAM), provides instructions and data to the processor 112. A portion of the memory 116 may also include non-volatile random access memory (NVRAM). The processor 112 typically performs logical and arithmetic operations based on program instructions stored within the memory 116. Therefore, the instructions in the memory 116 may be executable to implement at least part of the control and process methods of the system 100 described herein. The sterile medical device no may also include a non-illustrated digital signal processor (DSP) for use in processing signals. The sterile medical device no may include non-illustrated components such as, but not limited to, a power supply (e.g., a battery), a power switch (ON/OFF buttons), and other user-interface components as visual, tactile, and aural components for handling and operating such device.

The NFC tag 114 is a passive, preferably read-only device. The NFC tag 114 includes at least an antenna communicatively coupled to an integrated circuit (IC), and a memory. The NFC tag 114 can be any of an NFC® tag, an RFID® tag, a ZigBee® tag, or other like-technology tag embedded in the sterile medical device no and sealed inside a terminally sterile packaging 120. Medical device packaging must not only provide protection to the product, but it must also communicate what the product is, instructions, warnings and safety information, and other pertinent information such as; lot number, sterilization method, expiration date, etc. Sufficient space must be provided on the packaging for conveying this information either by printing directly on the package or by applying a label. Often, there must be also adequate space for the information in two or more languages. At least some of the above information could be provided within the memory of NFC tag 114. The sterile packaging 120 comprises, for example, a 3D printed package. And integrating the identification information about the sterile medical device 110 into the packaging 120 comprises, for example, adding a RFID tag, a NFC tag, or an electronic barcode, hologram or watermark encoded in an electronic circuit (smart labels), and combinations thereof into the 3D printed package which encloses the sterile medical device 110.

The packaging 120 can be of any material and shape conventionally known in the art. Conventional pouch and tray lid materials mainly consist of Tyvek®, foil and a few clear polymer variations. Conventional tray materials consist of polyethylene terephthalate glycol (PETG). PETG tends to be the most commonly used material, in particular for additive manufacturing (3D printing). PETG is transparent, has good mechanical properties and is compatible with the most common types of sterilization methods. Other materials may include polyvinyl chloride (PVC), polycarbonate (PC), polypropylene (PP) and high impact polystyrene (HIPS). For medical devices, materials and package validation testing is outlined in ISO standard 11607. Keeping in line with standard requirements, the packaging 120 may be a hermetically sealed container made of one or more different types of polymeric substrates or layers. In some embodiments, as mentioned above, the packaging 120 may be formed by 3D printing a container made of, for example, thermoplastic polyurethane (TPU), polyethylene terephthalate (PET). In other embodiments, the packing 120 may be made by a polymeric layer or layers of flexible material such as paper, synthetic paper, woven or non-woven sheets of medical grade fabric, polymeric film or sheets, and the like. In further embodiments, the packaging 120 can be made of extruded and molded polymer materials.

The non-sterile computing device 150 is, for example a general purpose computer or a modality's console computing resources including, among other things, a processor 152, a user interface 153, a NFC transceiver 154, a memory 156, and a wireless transceiver 158. The processor 152 controls all operations of the non-sterile computing device 150. The processor 152 may include a microprocessor which may also be referred to as a central processing unit (CPU), or may include other processor such as a field programmable gate array (FPGA) circuit board. Memory 156, which may include both read-only memory (ROM) and random access memory (RAM), provides instructions and data to the processor 152. A portion of the memory 156 may also include non-volatile random access memory (NVRAM). The processor 152 typically performs logical and arithmetic operations based on program instructions stored within the memory 156. The instructions in the memory 156 may be executable to implement at least part of the methods described herein. The user interface 153 provides user interface for the system 100 in general. The user interface 153 may provide an interface for a user (e.g., a doctor, a nurse, a technician, or the like) to communicate with the medical device 110. The user interface 153 may comprise a networked device, such as a tablet, a smart phone, a cellular phone, a laptop, or dedicated electronic hardware. The user interface 153 may be part of, or may be connected with, the non-sterile computing device 150, a healthcare facility intranet (e.g., a hospital intranet), or the sterile medical device 110 directly via physical wires, wirelessly, or both. The connection between the user interface 153 and the non-sterile computing device 150 or the sterile medical device 110 may be part of an in-room network. The user interface 153 may prompt the user to confirm treatment of a patient during a procedure, and once the user confirms, the user may scan NFC tag 114 of the medical device 110 before (or after) the packaging 120 of the sterile medical device is opened.

In the medical environment, prior to any use, the sterile medical device 110 must be paired with the non-sterile computing device 150 preferably before the seal on the sterile packaging 120 is broken. However, there can be events in which the pairing process may be required after the sterile packaging has been opened. The remainder of the disclosure provides detailed description of processes and algorithms which can be implemented by the processor 152 of the non-sterile computing device 150 and/or the processor 112 of the sterile medical device 110 to implement out-of-band pairing without compromising sterility thereof.
<FIG. 2>

Figure 2:
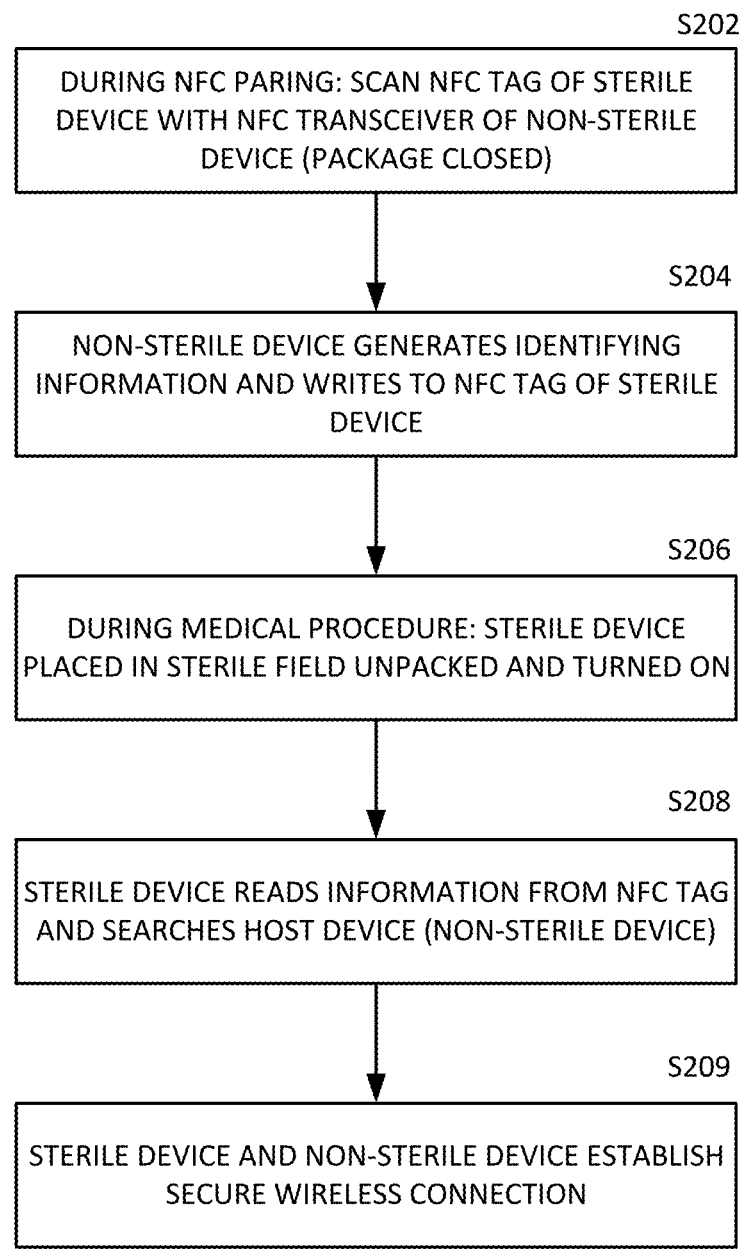
FIG. 2 is a flowchart of an exemplary process for paring a sterile medical device with a non-sterile computing device where, during pairing, the non-sterile device generates identification information and writes it into a NFC tag of the sterile device.

FIG. 2 is an exemplary flow diagram showing a process (method) of pairing the sterile medical device 110 with the non-sterile computing device iso, such as a computer, without compromising the sterility of the sterile medical device 110. In this embodiment, when the packaged sterile medical device no is brought within close proximity (near) the NFC transceiver 154 of the non-sterile computing device 150 (step S202), the NFC transceiver 154 transmits an inductive radiofrequency signal (an NFC signal 125) to the NFC tag 114 of the sterile medical device 110. More specifically, the NFC transceiver 154 of the non-sterile computing device 150 energizes an induction coil of the NFC tag 114. This transfer of energy causes the NFC transceiver 154 to transfer identification information, (e.g., an encryption key and/or a password) previously stored in memory 156 to the NFC tag 114 using NFC communication protocols (e.g., ISO/IEC 1800-3, ISO/IEC 18092/ECMA-340, ISO/IEC 21481/ECMA-352). That is, according to one embodiment, the non-sterile computing device 150 generates and writes identifying information into the NFC tag 114 of the sterile medical device 110 (step S204).

The "identifying information" includes, but is not limited to, a wireless identifier, a password/passkey, and/or an encryption key necessary for exchanging information between the sterile medical device 110 and the non-sterile computing device 150. A wireless identifier may include, for example, a SSID (service set identifier), a MAC (media access control) address, an IP (internet protocol) address, a UUID, BD_ADDR value, OUI (organization unique identifier), etc., as it is known to persons skilled in the art. In order to ensure safety, prior to writing the identifying information into the NFC tag 114 of the sterile medical device 110, it is preferable that the NFC tag 114 is empty. To that end, the NFC tag 114 can be configured to accept and store new identifying information from an NFC writer (e.g., the NFC tag can be rewritable).

More specifically, at step s202, the NFC tag 114 of the sterile medical device 110 is scanned by the NFC transceiver 154 of the non-sterile computing device 150. At step S204, the processor 152 of the non-sterile computing device 150 executes an appropriate software application to read (form memory 156) or generate identifying information, and to write the identifying information into the NFC tag 114 of the sterile medical device 110. After the sterile medical device 110 has been paired (registered) with the non-sterile computing device iso, the user (e.g., a physician) may proceed to a sterile area (e.g., an operating room) where the packaging 120 of the sterile medical device no can be opened and activated (powered ON) for use. When the sterile packaging 120 is opened, and the sterile medical device 110 is turned on (step S206), the sterile medical device 110 can read (use) the identifying information 125 contained in the NFC tag 114 (step S208) to search for a host device. Specifically, the sterile medical device no reads the identifying information from the NFC tag 114, and uses that identifying information (e.g., the identity of the non-sterile device) to securely establish wireless communication 135 with the non-sterile computing device 150 (step S209). The wireless communication 135 preferably occurs over a secondary communication protocol different than the NFC protocol, such as Bluetooth, Direct WiFi, wireless local area network (wireless LAN), or the like.

In other words, as described above, the NFC protocol may be used for out-of-band pairing between the NFC tag 114 of the sterile medical device 110 and the NFC transceiver 154 of the non-sterile computing device 150. On the other hand, wireless communication 135 between the sterile medical device 110 and the non-sterile computing device 150 uses a communication protocol having a higher bandwidth and/or longer range than the short-range (near field) of the NFC protocol.

Out-of-band pairing of the NFC tag 114 of the sterile medical device 110 with the NFC transceiver 154 of the non-sterile computing device 150 may use any of various suitable short-range wireless communication technologies, besides NFC protocol, such as Bluetooth short-range, RFID, ZigBee (IEEE 802.15.4, IEEE 802.15.4a), ANT/ANT+, body area networks (BAN) protocols, Medical Implant Communication Service (MICS), 6LoWPAN, and the like. The wireless communication 135 between the sterile medical device no and the non-sterile computing device 150 may use longer range communication technologies, such as Bluetooth Low Energy (BTLE), WiFi in accordance with the IEEE 802.11 standard, Bluetooth High Speed, Direct WiFi, Ultra Wide Band (UWB), and the like. For maintain high security, the wireless communication between the sterile medical device 110 and the non-sterile computing device 150 (signal 135) may be a point-to-point connection, such that the data transferred between the two devices will not have to travel via a large network or the Internet.

An example of the Bluetooth out-of-band short-range carrier is described, for example, in Bluetooth Specification, Version 4, Jun. 30, 2010. An example of the Radio Frequency Identification (RFID) out-of-band short-range carrier is described, for example, in ISO 11785 (air interface protocol), ISO 14443 (air interface protocol), and ISO 15693. An example of the Near Field Communication (NFC) out-of-band short-range carrier is described, for example, in ISO/IEC 14443 and ISO/IEC 18092.

Referring back to FIG. 1, the NFC tag 114 is a passive, read-only device, fabricated on a thin substrate (e.g., like a sticker). The NFC tag 114 includes at least an antenna communicatively coupled to an integrated circuit (IC), and a memory configured to store at least identification information (e.g., a number, a code, a key, a password, etc.) for identifying the sterile medical device 110 to which it is attached. The NFC tag 114 can be configured to be written-to only once or multiple times to its memory. Moreover, the NFC tag 114 can be programmed (written) during manufacture and/or preferably after integration into the sterile medical device 110 (e.g., when the tag is already attached to the sterile medical device 110). The write operation to the NFC tag 114 can be accomplished using a passkey or other secure method into an area where further write operations can be prevented unless the passkey is known. The NFC tag 114 preferably does not include any power source. Instead, NFC tag 114 draws power from the NFC transceiver 154 which reads and/or writes to NFC tag 114 using magnetic induction. In this manner, the NFC tag 114 can be manufactured with reduced size in a small form factor, and at a minimum cost.

The NFC tag 114 can store additional information (e.g., information aside from identification information required for pairing) that can be transferred to the non-sterile computing device 150 via the NFC protocol, including but not limited to a serial number, an identification type/model/manufacturer of the sterile medical device 110. The NFC tag 114 can store unique information that identifies an authentic sterile medical device 110 over a counterfeit (possibly non-sterile) device. Furthermore, the NFC tag 114 can be configured to store information indicative of whether the sterile medical device 110 has been previously used (e.g., information indicative of whether sterility has been breached). For example, the NFC tag 114 can be programmed with an inductive or capacitive flag that can be activated once the NFC tag 114 has been scanned with an NFC reader. In this manner, the NFC tag 114 may provide an indication of whether or not sterility of the medical device has been compromised.

In the present disclosure, although NFC tag 114 is described as a passive tag which can be manufactured with reduced size in a small form factor and at a minimum cost, it will be a matter of design choice to provide the NFC tag 114 as an active tag, if desired. Similar to NFC passive tags, a NFC active tag has an IC, an antenna and memory, but it also has an on board power supply and on board reader/writer circuit, which allows the NFC tag to actively broadcast signals and transfer data. NFC tags are manufactured in a variety of form factors and functional types. Although, most NFC tags communicate using the ISO 14443 type A and B wireless standards over the 13.56 MHz NFC transmission frequency, each type of NFC tag provides a different storage capacity and transfer speed. Tag types 1 and 2 come with capacities between 48 bytes and 2 kilobytes of data, and can transmit that information at 106 Kbps (kilo-bits-per-second). Type 3 NFC tags use the Sony Felica standard, and can transfer data at 212 Kbps. Type 4 NFC tags have a larger memory capacity of up to 32 Kbytes and communication speeds of between 106 to a maximum of 424 Kbps. NFC tags types 1 and 2 can be rewritten and reused, while types 3 and 4 are read only and cannot be rewritten.

<FIG. 3>

Figure 3:
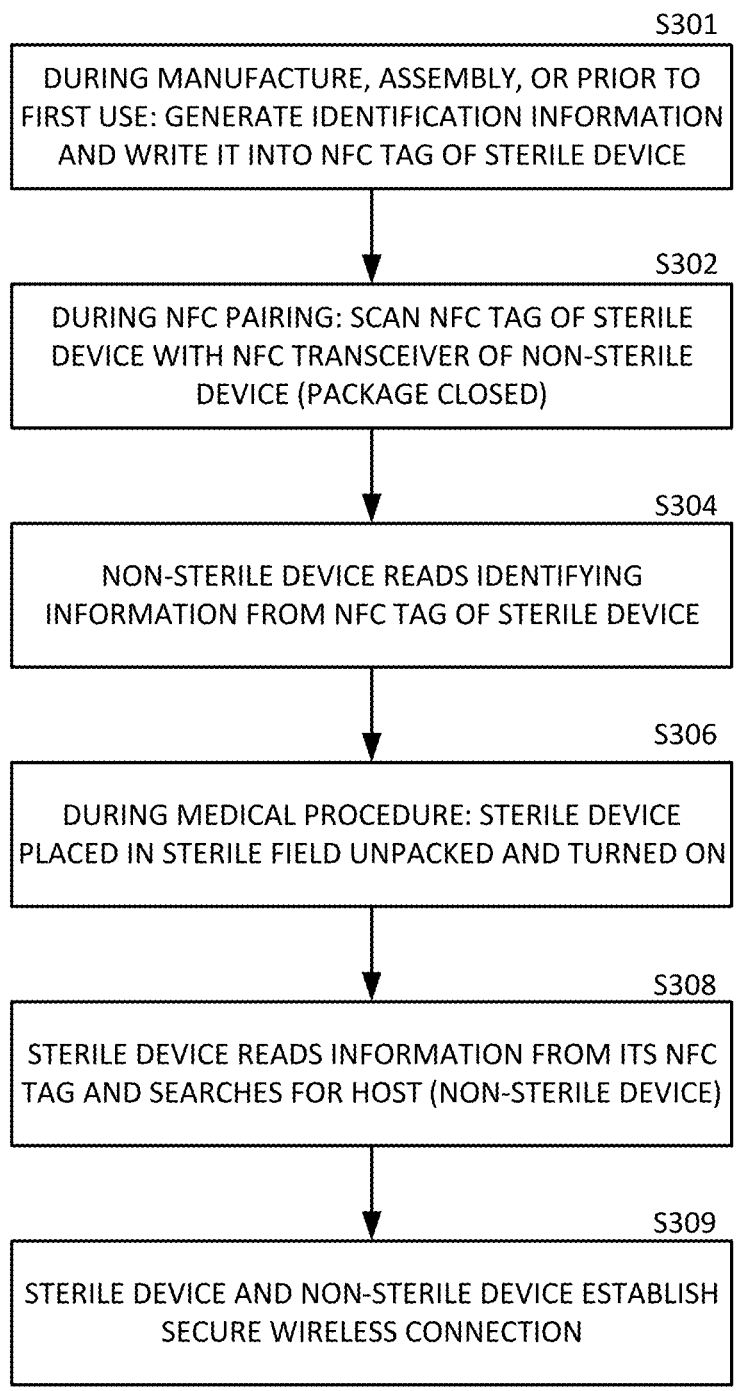
FIG. 3 is a flowchart of an exemplary process for paring a sterile medical device with a non-sterile computing device wherein, during manufacturing, identification information is written into the NFC tag of the sterile device.

Turing now to FIG. 3, another pairing method is described. According to FIG. 3, a method of pairing a sterile medical device 110 with a non-sterile computing device 150 includes generating and writing sterile device identifying information to the NFC tag 114 during manufacturing.

Specifically, according to the process illustrated in FIG. 3, at step S301, during manufacture and/or assembly of the sterile medical device 110, a non-illustrated NFC writer is configured to generate and write identification information into the NFC tag 114 of the sterile medical device 110. As noted above, the NFC tag 114 may be programmed with a serial number, an identification type/model/manufacturer of the sterile medical device 110, and/or identification information required for pairing.

Then, at step S302, when the sterile medical device 110 is scanned in its package 120 with the NFC transceiver 154 of the non-sterile computing device 150. At step 304, the non-sterile computing device 150 will receive (read) this information and store it in its memory 156. During a medical procedure, once the sterile medical device 110 is unpackaged and turned on (step S306), the sterile medical device 110 will read (S308) the information stored on its NFC tag 114 during manufacturing, and searches for a host (the non-sterile device). Once the host is found, sterile medical device 110 will start secure wireless communications (S309) with the non-sterile computing device 150 over a secondary communication protocol such as Bluetooth or Direct WiFi utilizing the information previously stored in the NFC tag 114.

In this case, when the identification information is stored into the NFC tag 114 of the sterile medical device 110 during manufacture, it may be possible that an authorized NFC reader may tamper with (read) the sterile medical device 110. To prevent such possibility, an embodiment of the present disclosure provides an added level of security.

<FIG. 4>

Figure 4:
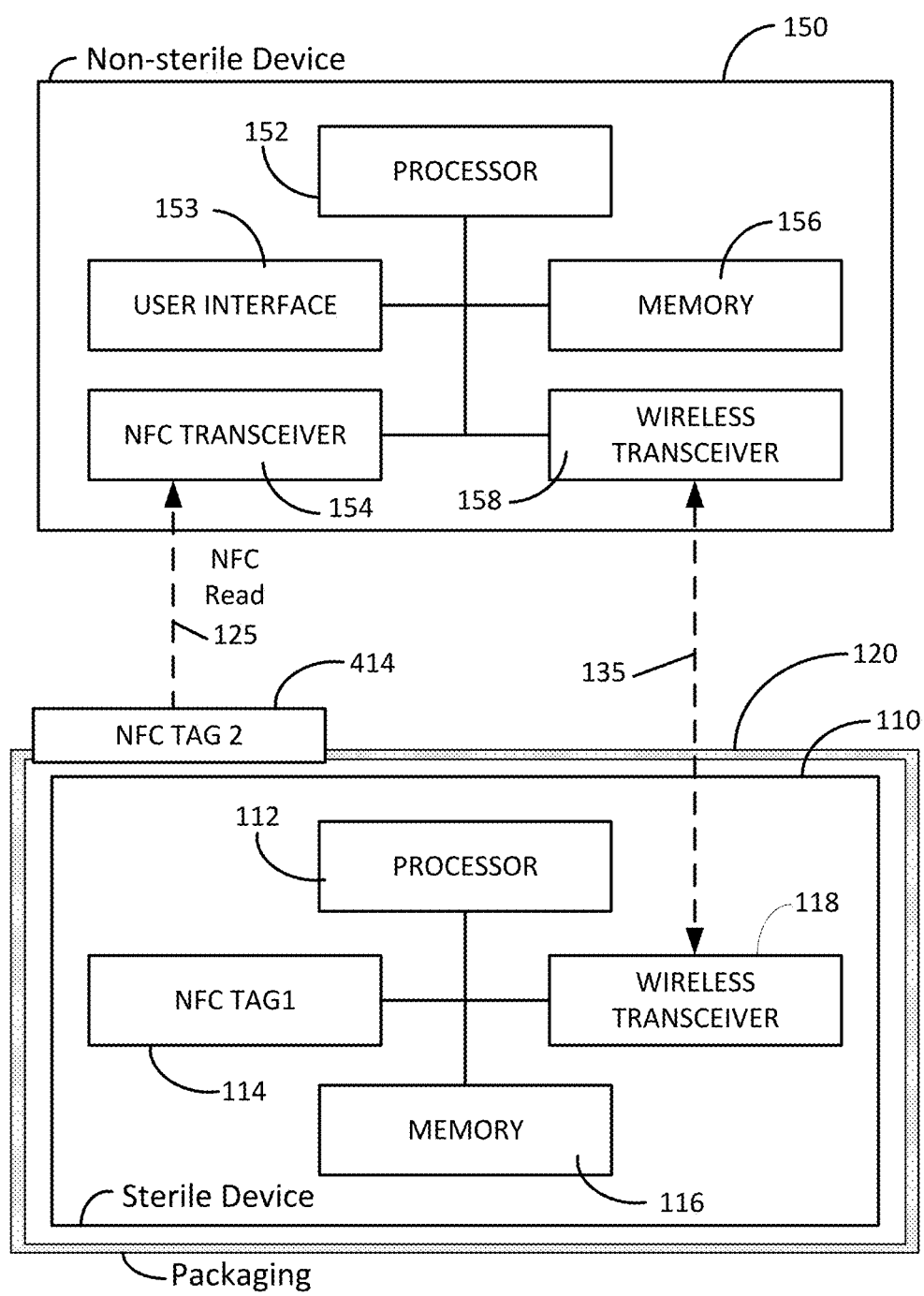
FIG. 4 is a diagram of an exemplary system for paring a sterile medical device with a non-sterile computing device using short-range near field communication protocols.

FIG. 4 illustrates an embodiment of a system for pairing a sterile medical device 110 with a non-sterile computing device 150 without compromising sterility of the sterile medical device. In the previous embodiment, if the sterile packaging 120 were accidentally or intentionally opened before the pairing procedure, the sterile medical device 110 could not be paired with the non-sterile computing device 150 without compromising sterility, which would render the sterile medical device 110 potentially inoperable. In addition, if the NFC tag 114 was read or written by an authorized NFC transceiver, the sterile medical device 110 could not be paired with the non-sterile computing device 150. The embodiment of FIG. 4, addresses these issues by embedding a secondary NFC tag 414 in the packaging 120 of the sterile medical device 110.

More specifically, the embodiment illustrated in FIG. 4 is structurally similar to the system shown in in FIG. 1. However, in FIG. 4, the system 100 includes a sterile medical device 110 enclosed in a sterile packaging 120, wherein the sterile medical device 110 includes an embedded first NFC tag 114 (NFC TAG1), and the sterile packaging 120 includes a second NFC tag 414 (NFC TAG2). All other aspects of the system 100 shown in FIG. 4 are the same as that of the system 100 shown in FIG. 1.

In FIG. 4, the first NFC tag 114 is non-removably embedded or integrated with the sterile medical device 110. On the other hand, the second NFC tag 414 can be affixed to the packaging 120 (in the inside or outside surface), or it can be loose in the packaging 120, or it can be a detachable sticker removably affixed to the sterile medical device 110 and fixedly attached to the packaging 120. If the second NFC tag 414 is embedded in the packaging 120 and at the same time connected or removal affixed to the sterile medical device 110, when the sterile medical device no is removed from the packaging 120, the second NFC tag 414 remains attached to the packaging 120.

From henceforth the second NFC tag 414 may also be referred to as the packaging NFC tag. In this embodiment the packaging NFC tag will be read (scanned) by the NFC transceiver 154 of non-sterile computing device 150. To avoid that an authorized NFC reader may tamper with the sterile medical device 110, the packaging NFC tag (the second NFC tag 414) and the first NFC tag 114 can be programmed during device manufacture and must contain the same specific identifying information of the sterile medical device 110. During device pairing, the NFC transceiver 158 of the non-sterile computing device 150 will read the information stored in the second NFC tag 414 using the short-range NFC protocol; this allows the non-sterile computing device 150 to establish a secure connection over another wireless communication protocol such as Bluetooth, wireless local area network (WLAN), or Direct WiFi.

Specifically, the non-sterile computing device 150 can employ known authorization/authentication methods to facilitate pairing with the sterile medical device 110 via NFC protocol. For example, during manufacturing, the NFC tag 114 can be programmed with identification information that uniquely identifies the sterile medical device 110 to the non-sterile computing device iso. During the pairing process, the NFC transceiver 154 can read (scan) the second NFC tag 414, and store the read information in memory 156. Then, the non-sterile 150 can compare the identification information read from the NFC tag 414 with identification information stored in NFC tag 114. Since information stored in NFC tag 114 will match the identification information read from the NFC tag 414, the non-sterile device 150 and the sterile medical device no can establish a secure communication link over a long-range and high-speed communication protocol, such as Bluetooth or the like.

<FIG. 5>

FIG. 5 illustrates a method of pairing a sterile medical device 110 with a non-sterile computing device 150, as those shown FIG. 4, without compromising sterility of the sterile medical device 110. In this embodiment, at step S501, during manufacturing and/or assembly, identification information unique to the sterile medical device no is generated and written into both the first NFC tag 114 of the sterile medical device 110 and into the second NFC tag 414 of the sterile packaging 120. As discussed elsewhere in the disclosure, it is also possible to leave the first and second tags blank during manufacture/assembly, and then write paring information from the non-sterile device 150 into the first NFC tag 114 and the second NFC tag 414 at the time of first use in a medical operation. At step S502, in the event that the user may intentionally or accidentally break the sterile seal and separate the sterile medical device 110 from its packaging 120, the sterile medical device 110 can preserve its sterility while the packaging 120 is used for pairing with the non-sterile computing device 150. Specifically, at step S503, the NFC transceiver 154 scans the second NFC tag 414 of the sterile packaging 120. Then, at step S504, the NFC transceiver 154 reads the identifying information from NFC tag 414, and stores the identification information in memory 116.

The process of steps S504, S506, S508, and S509 are similar to the previously described steps S204, S206, S208, and S209 of FIG. 2.

In the present embodiment, the benefit offered by the second NFC tag 414 is that the packaging tag does not need to remain sterile, and thus it can be scanned in the non-sterile environment with the non-sterile computing device 150 even if the packaging of the sterile device is opened (accidentally or otherwise). Naturally, before opening the sterile packaging either NFC tag 114 of the sterile medical device 110 or the second NFC tag 414 of the packaging 120 can be scanned with the computer to initiate wireless pairing. If the packaging 120 is opened before pairing, then the NFC tag 414 contained in the packaging can be brought out of the sterile field and scanned with the non-sterile computer thus preserving the sterility of the sterile medical device 110.

The first NFC tag 114 of the sterile medical device 110 could be eliminated completely and a duplicate of the identifying information stored in the NFC tag 414 of the packaging 120 could be hard coded into the memory 116 of the sterile medical device 110 as an alternative embodiment. However, maintaining the two tags (a first NFC tag 114 and a second NFC tag 414) has a major benefit in the device manufacturing process because this allows for the packaging NFC tag (the second NFC tag 414) to be programmed after the device is mated with its corresponding sterile enclosure.

<FIG. 6>

Figure 6:
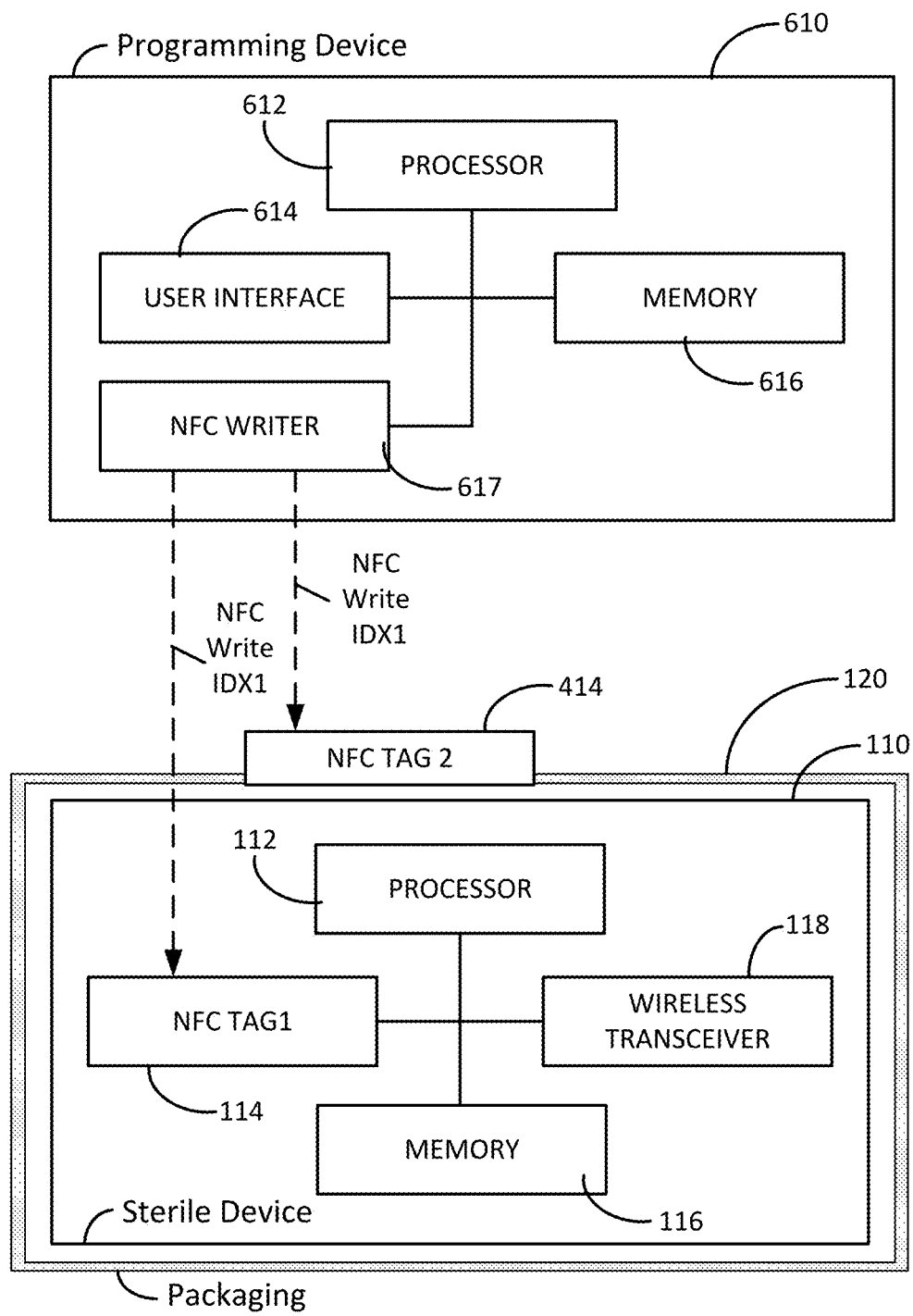
FIG. 6 is a diagram of an exemplary system for preprogramming, during manufacturing, identification information into a NFC tag of the sterile device and into a NFC tag of the sterile packaging.

FIG. 6 is a diagram of an exemplary system for preprogramming, during manufacturing, identification information into a NFC tag of the sterile device and into a NFC tag of the sterile packaging. In FIG. 6, the system includes a manufacturing programming device 610 configured to program the first NFC tag 114 of the sterile medical device 110 and the second NFC tag 414 of the packaging 120. To that end, the manufacturing programing device 610 includes a processor 612, a memory 616, a user interface 613, and a NFC writer 617. In this case, the manufacturing programming unit 610 uses the NFC writer 617 to program (write into) both the sterile device NFC tag 114 and the packaging NFC tag 414 with the same (duplicate) identification information IDX1. The processor 612, memory 616 and user interface 613 are similar to processor 152, memory 156 and user interface 153, respectively, of the non-sterile device 150.

<FIG. 7>

Figure 7:
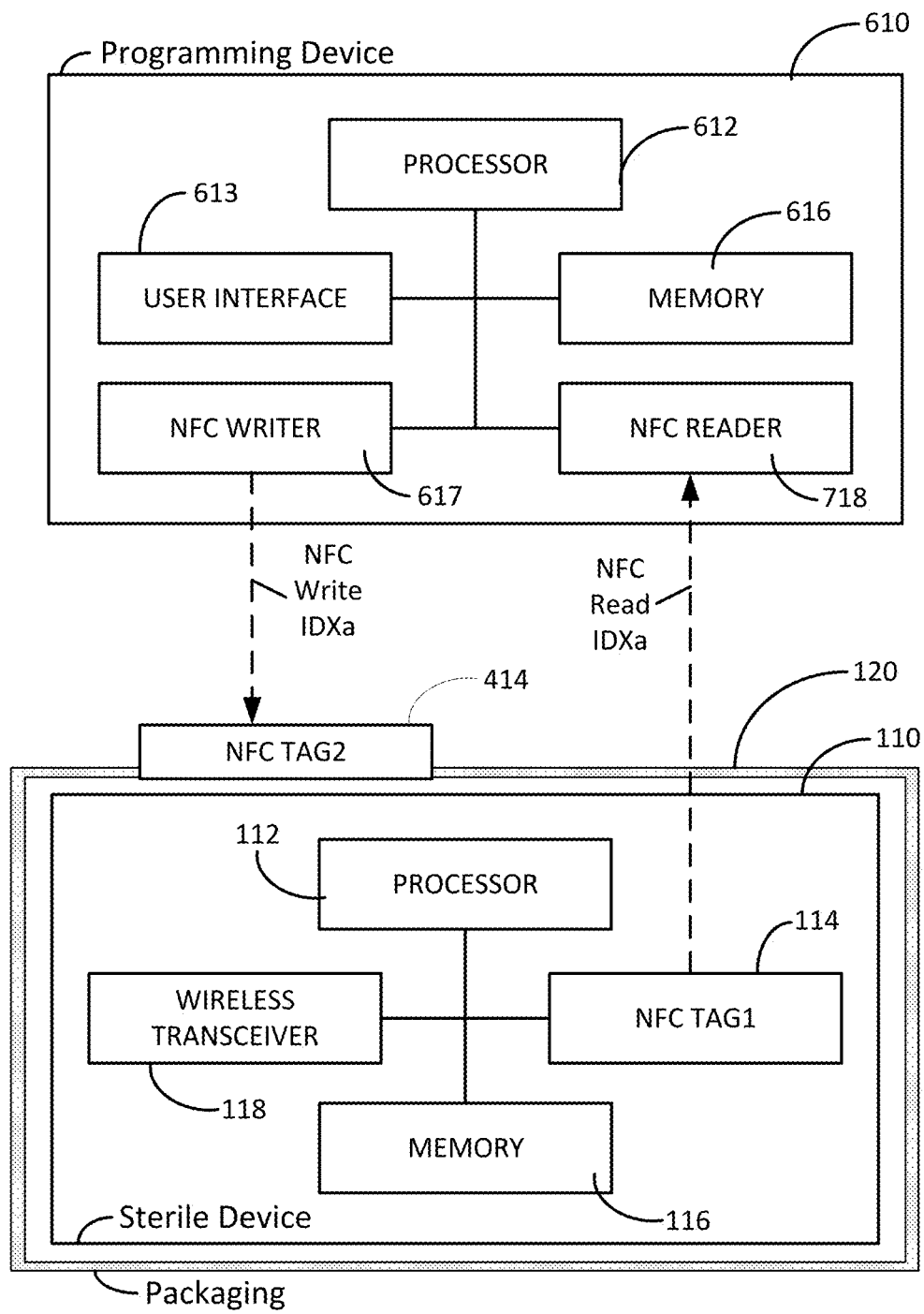
FIG. 7 is a diagram of an exemplary system for duplicating identification information preprogrammed in the NFC tag of the sterile device onto the NFC tag of the sterile packaging.

FIG. 7 is a diagram of an exemplary system for duplicating identification information preprogrammed in the NFC tag 114 of the sterile medical device no onto the NFC tag 414 of the sterile packaging 120. In FIG. 7, it is assumed that the sterile medical device no has previously generated and stored identifying information already programmed into its NFC tag 114. This could occur during the manufacturing of sterile medical device no, or during functional testing thereof, for example. In this case, during assembly (mating) of the sterile medical device no with its packaging 120, the manufacturing programming device 610 reads the NFC tag 114 (NFC tag 1) of sterile medical device no to extract the identifying information already stored therein, and duplicates such information onto the packaging NFC tag 414. More specifically, as shown in FIG. 7, the NFC reader 718 of the manufacturing programming device 610 reads identification information (IDXa) from the NFC tag 114. Then, the NFC writer 617 writes the same identification information (IDXa) into the NFC tag 414 of the packaging 120.

Both methods shown in FIGS. 6 and 7 allow for the packaging NFC tag (NFC tag 114) to be programmed during or after the sterile medical device no is mated with its corresponding packaging 120. The benefit of programing the NFC tag 114 and the NFC tag 414 with the same information is the reduced risk of mismatch between the sterile device NFC tag and the packaging NFC tag. Since NFC tags 114 and 414 work under wireless near field technology, the tags can be programmed after the packaging is sealed, and if desired even after the device has been sterilized.

When the NFC tags are programmed during device manufacture, the information contained on the NFC tag could be available to be read and/or tampered with by a nefarious user (man-in-the-middle), e.g., during device transport to a medical facility. A nefarious user could utilize the information contained on the NFC tags to perform a man-in-the-middle (MITM) attack of the wireless communication between the devices. The paring process of FIG. 2 is more secure since the identifying information is only written to the NFC tag when the device is ready to be used. Embodiment 3 is a method of embodiment 2 coupled with additional security enhancements to prevent MITM attacks.

<FIG. 8>

Figure 8:
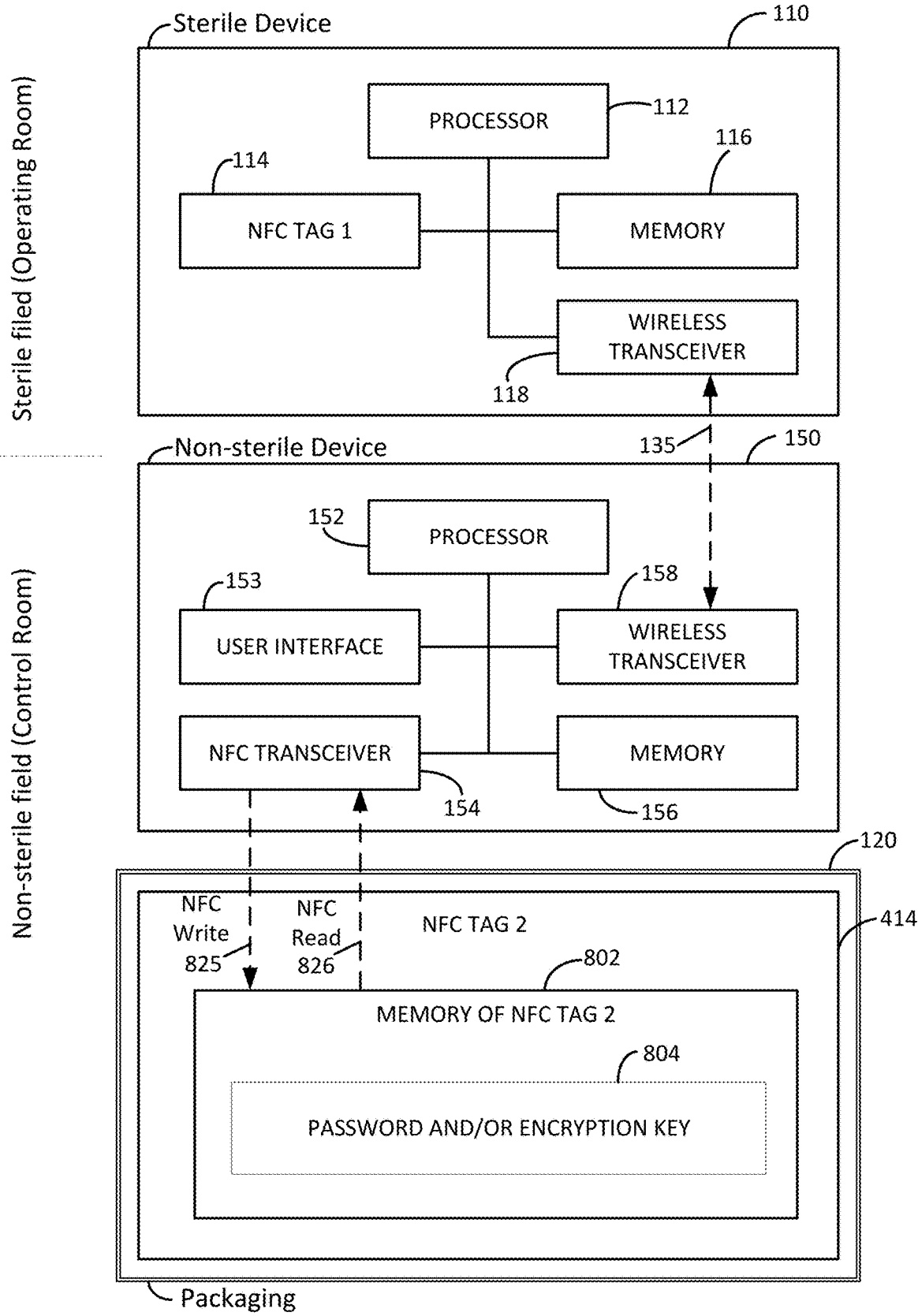
FIG. 8 is a diagram of an exemplary system and method for encrypting or password protecting the NFC tag of the package and the NFC tag of the sterile device.

FIG. 8 illustrates a system and method in which the NFC tag 414 of the package 120 and the NFC tag 114 of the sterile device 110 are either password protected and/or pre-encrypted. Specifically, as shown in FIG. 8, during a medical procedure, the packaging 120 is first separated from the sterile medical device 110 intentionally or otherwise. The NFC tag 414 (NFC TAG2) of the packaging 120 includes a memory 802 which has been preprogrammed with a password and/or an encryption key (identifying information 804).

To initiate sterile device use (during a medical procedure), the NFC transceiver 154 of the non-sterile computing device 150 will communicate the identifying information (password/key) to the NFC tag 414, by a NFC write command 825. In this manner, the NFC tag identifying information 804 is unlocked for reading by the non-sterile device 150 via a NFC read command 826. This process makes the sterile device 110 more secure because a nefarious user would require knowledge of this preprogrammed password/key in order to read the information contained on the NFC tag 414 of the packaging 120. Thus, preprograming the NFC tag 414 with identifying information 804 provides an additional layer of security.

Alternatively, the method includes adding identifying information stored on the NFC tags pre-encrypted with a common (the same) key (e.g., as shown in FIG. 6). To that end, it is preferable that the manufacturer has control over the programming of both the sterile device 110 and non-sterile device 150, so that the manufacturer can implement a proprietary encryption algorithm on both devices. When the identification information stored in the NFC tags is read by the non-sterile device, the identifying information could be decrypted with the pre-stored key, and then the decrypted information will be used to secure wireless communications between the sterile device and the non-sterile device. A nefarious user would be required to reverse engineer the encryption algorithm contained on the sterile or non-sterile device to perform a MITM attack of the wireless communications. However, in order to practice this method, the same programming (preferably by the same manufacturer) would need to be done on both sterile and non-sterile devices so that both devices know the correct key to negotiate secure communications.

Lastly, a higher security method of pairing a sterile medical device to a non-sterile computing device would combine the method of using a password with the method of using an encryption key. A combination method for higher security includes storing a pre-encrypted key on both NFC tags (i.e., in the first NFC tag 114 and in the second NFC tag 414). In addition, the combination method includes providing a common password (the same password) that would unlock both NFC tags (i.e., in the first NFC tag 114 and in the second NFC tag 414). In this manner, the NFC tags are both encrypted with a key, and password protected. In this combination method the non-sterile device 150 would transmit a password to the NFC tag 414 thus unlocking its contents to be read. The non-sterile device 150 would then read the pre-encrypted key from the NFC tag 114 of the sterile device 110. The pre-encrypted key would then be run through a proprietary decryption algorithm to discover the actual key that will be used to encrypt wireless communications. Since this method provides several layers of security it can be considered the maximum security method to practice while still maintain the sterility of the sterile medical device.

This disclosure has the following advantages over conventional art. All of the embodiments allow for secure out-of-band pairing of a sterile device to a non-sterile device without sterility of the sterile device. One or more embodiments provides a mode for programming sterile devices after they are mated with their packaging and sterilized in manufacturing reducing the risk of mismatch of packaging and device. One or more embodiments provide additional security measures to reduce the risks of unauthorized usage, MITM attacks, and/or tampering of sterile medical devices.

A novel system and methods for out-of-band pairing of a sterile device to a non-sterile device are disclosed. In one aspect, the sterile device is provided with an embedded NFC tag; the NFC tag and the sterile device are enclosed in a sterile package. A secondary NFC tag is provided in the sterile packaging of sterile medical device. This enables pairing the sterile device with a non-sterile device even after the sterile barrier packaging is opened, but without compromising the sterility of the sterile device. According to one aspect, a method includes programming of the packaging NFC tag and sterile device NFC tag after the sterile device is mated and sealed with its package and sterilized. This allows for the programming to be performed with custom processes or algorithms by entities other than the manufacturer.

At least one embodiment includes the above features plus password protected NFC memory for added security. At least one embodiment includes the above features plus pre-encoded wireless device information and encryption key for additional security to further reduce the probability of MITM attacks. At least one embodiment includes the above features plus password protected NFC memory and pre-encoded wireless device information and encryption key.

Thus far, the disclosure has described various aspects of pairing a sterile device with a non-sterile device for wireless communications. Several environments to practice the various novel aspects are included herein.

<FIG. 9>

Figure 9:
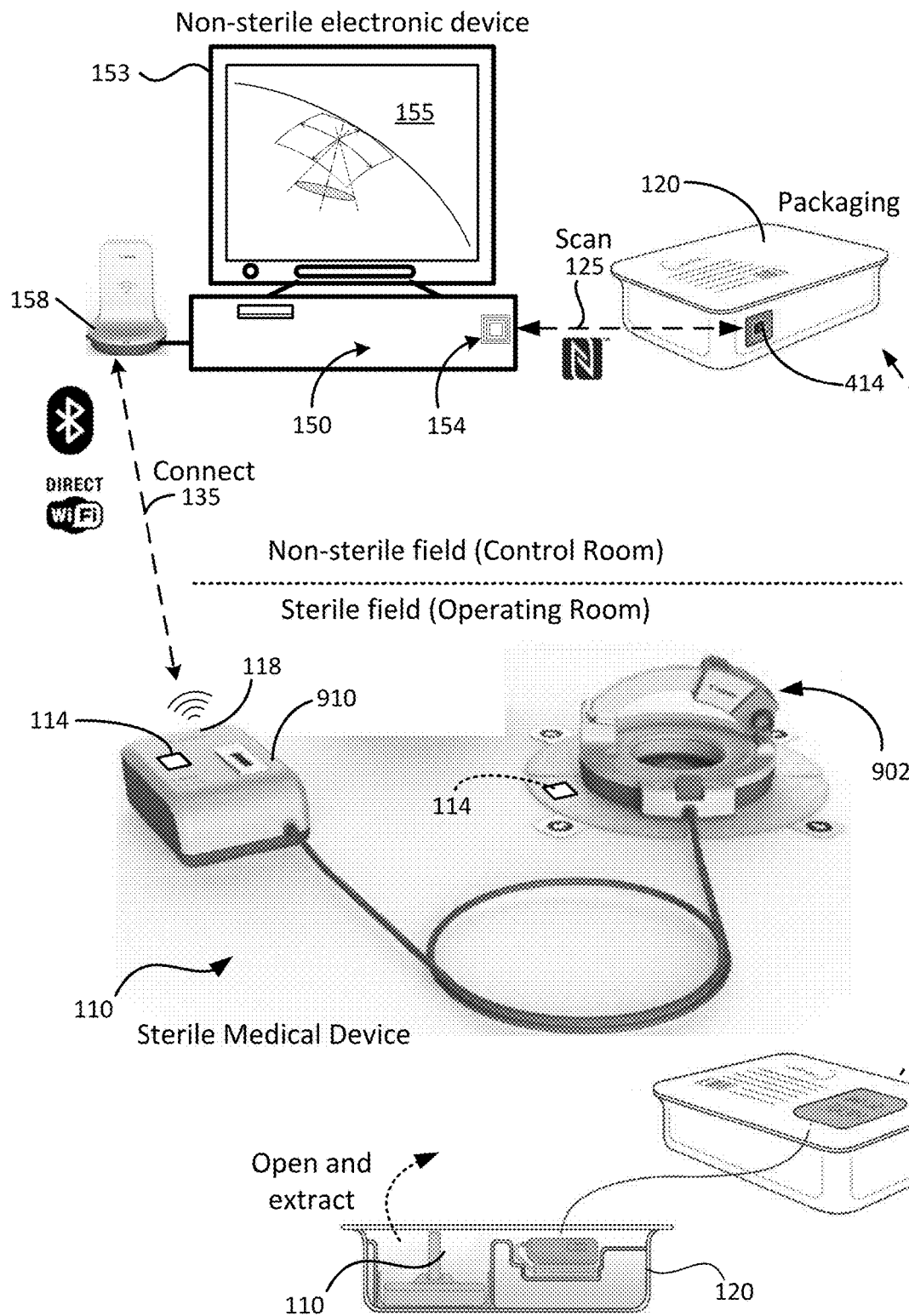
FIG. 9 is a diagram of an exemplary system for pairing a sterile percutaneous needle guidance device with a non-sterile computer without breaking sterility of the sterile percutaneous needle guidance device.

FIG. 9 is a diagram of an exemplary system for pairing a sterile percutaneous needle guidance device with a non-sterile computer without breaking sterility of the sterile percutaneous needle guidance device. In the example of FIG. 9, a sterile medical device 110 needs to pair and communicate with a non-sterile computing device 150. The sterile medical device no includes, for example, a sterile guidance device 902 and a sterile communication unit (CU) 910. The non-sterile computing device 150 includes, for example, a computer or system console equipped with a wireless communication transceiver 158 (e.g., a WiFi router or access point), a near-filed or NFC transceiver 154, and a display device 153. The display device 153 can be a touch-screen liquid crystal display (LCD) which displays images and medical operations on a graphical user interface (GUI) 155.

The sterile guidance device 902 is a sterile needle-guiding instrument which includes or is connected to the communication unit (CU) 910. The communication unit 910 and/or the guidance device 902 have an embedded NFC tag 114 (at least one first NFC tag). Prior to use in a medical procedure, this guidance device 902 and communication unit 910 are packaged in a sterile packaging 120. The packaging 120, in turn, also contains an attached or embedded NFC tag 414 (a second NFC tag). The NFC tag 414 contains identification information which is a duplicate of identification information contained in the NFC tag 114 of the sterile medical device 110. Before opening the sterile packaging 120 either the first or second NFC tag (114 or 414) can be scanned with the NFC transceiver 154 of the non-sterile computer device 150 to initiate OOB pairing using a NFC signal 125 under NFC communication protocol (refer to FIG. 10A). After pairing, the sterile packaging 120, which still contains the sterile medical device is moved to the sterile field and opened (as shown in FIG. 10B) to prepare the guidance device 902 and communication unit 910 for use (refer to FIG. 10C-FIG. 10D). If the package 120 is first opened in the sterile field (e.g., operating room) before pairing, then the NFC tag 414 contained in the now empty packaging 120 can be brought out of the sterile field (see arrow 913 in FIG. 9), and scanned with the NFC transceiver 154 of the non-sterile computer device 150 thus preserving the sterility of the guidance device 902 and of the communication unit 910. Upon reading the NFC tag 414 by the NFC transceiver 154, the non-sterile device 150 stores the identification information in its memory 156. When the sterile medical device no is powered ON, communication unit 910 reads information from the NFC tag 114 and searches for a host device (non-sterile device 150). Since the host device can confirm the identification information of NFC tag 114, the communication unit 910 establishes a secure connection with the wireless transceiver 158 of the non-sterile computing device 150 via a wireless signal 135 under a communication protocol other than the NFC protocol, e.g., Bluetooth or Direct WiFi or other similar longer range communication protocol.

<FIG. 10>

Figure 10A:
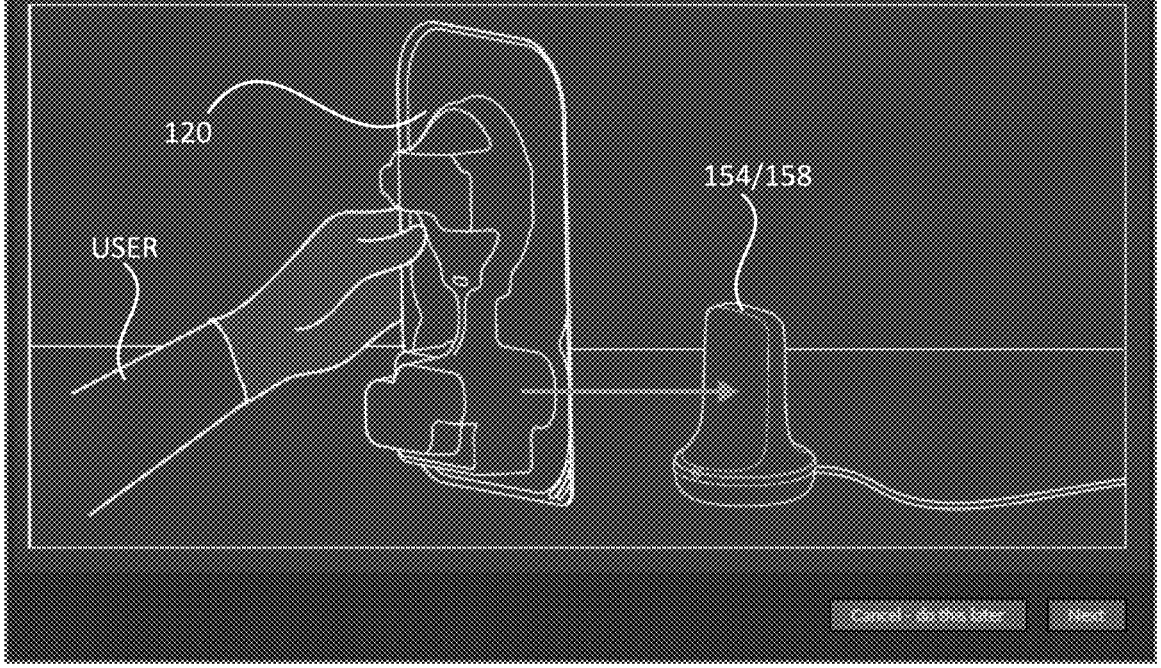
FIG. 10A through FIG. 10E show exemplary GUI prompts for guiding a user to perform a process of pairing a sterile percutaneous needle guidance device with a non-sterile computer without breaking sterility of the sterile percutaneous needle guidance device.
Figure 10B:
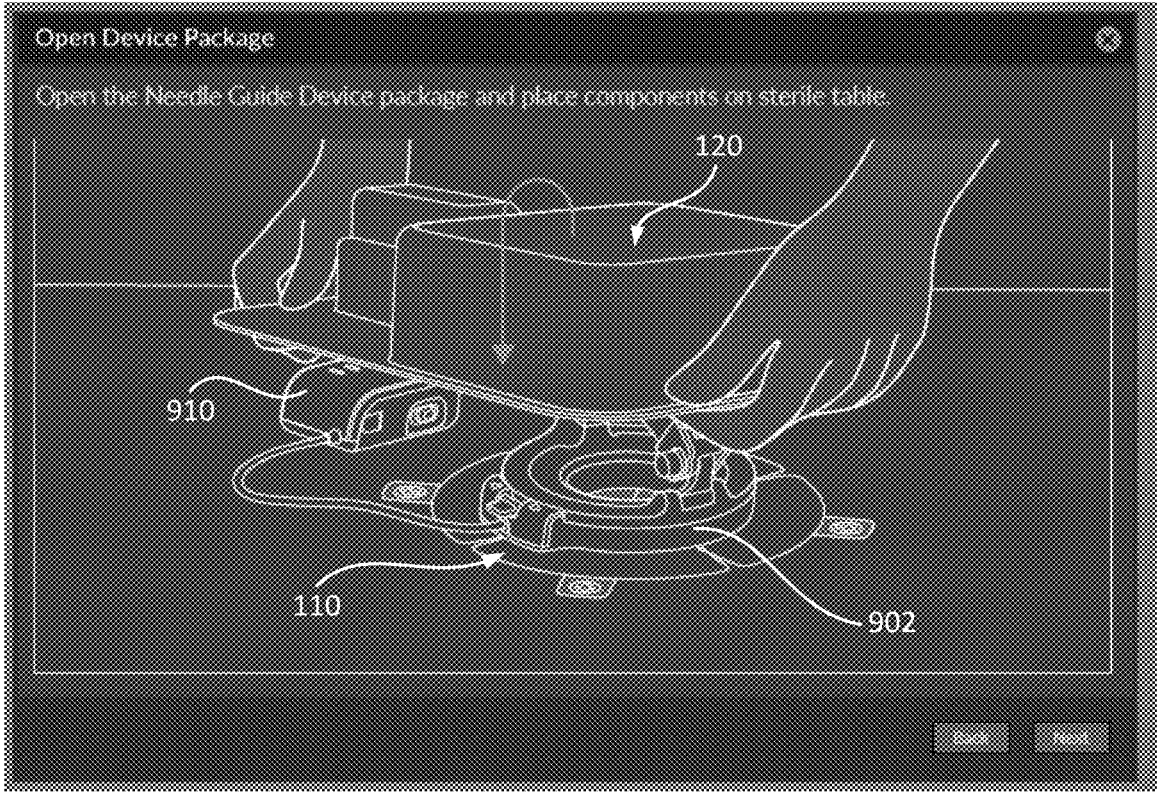

FIG. 10A through FIG. 10E show exemplary GUI prompts for guiding a user to perform a process of pairing a sterile percutaneous needle guidance device with a non-sterile computer without breaking sterility of the sterile percutaneous needle guidance device. As shown in FIG. 10A, prior to initiating a medical procedure which requires the use of a sterile medical device 110, the system console or non-sterile computer device 150 can be configured to prompt a user, via the GUI 155, to scan the sterile medical device 110 (in this case a needle guide device) using a reader (e.g., NFC transceiver 154) attached to the computer device 150. Here, the system console or computer device 150 can be programmed to prompt the user to move or place the packaged sterile medical device in a specific manner (e.g., at a specific position, distance, or orientation) until the sterile medical device is effectively scanned by the console reader.

Figure 10C:
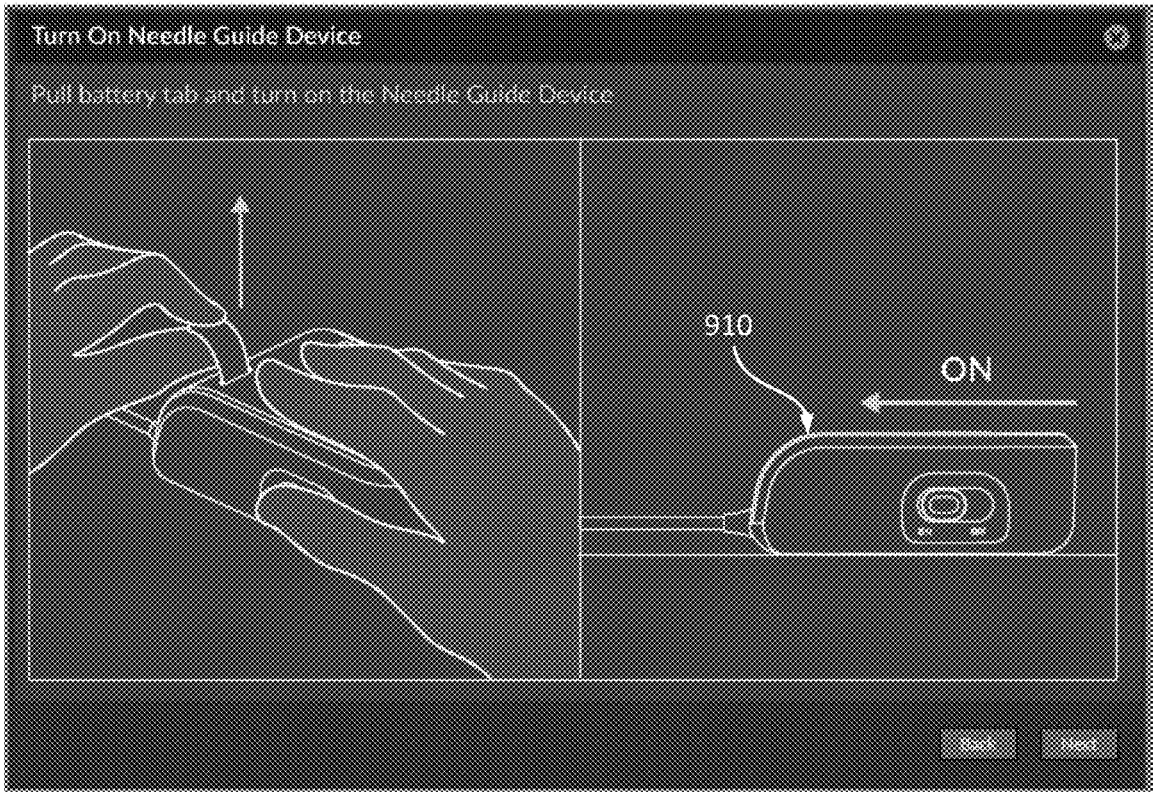

As shown in FIG. 10B, the computer device 150 can be further programmed to prompt the user to open the device page, and place the sterile device components on a safe environment of the sterile field (e.g., a sterile table). As shown in FIG. 10C, the computer device 150 can be further configured to prompt and instruct the user, via the GUI 155, how to activate (turn ON) the sterile medical device 110. As explained earlier, when the sterile medical device 110 is activated (turned ON), the communication unit 910 reads identification information from the NFC tag 114, and starts searching for a host device (non-sterile device). Here too, in the case that the sterile device 110 does not find a host device, the computer device 150 can be programmed to prompt the user, via the GUI 155, to move or reposition the unpackaged sterile medical device 110 in a specific manner (e.g., at a specific position, distance, or orientation) until the sterile medical device 110 establishes reliable wireless communication with the non-sterile device iso.

Figure 10D:
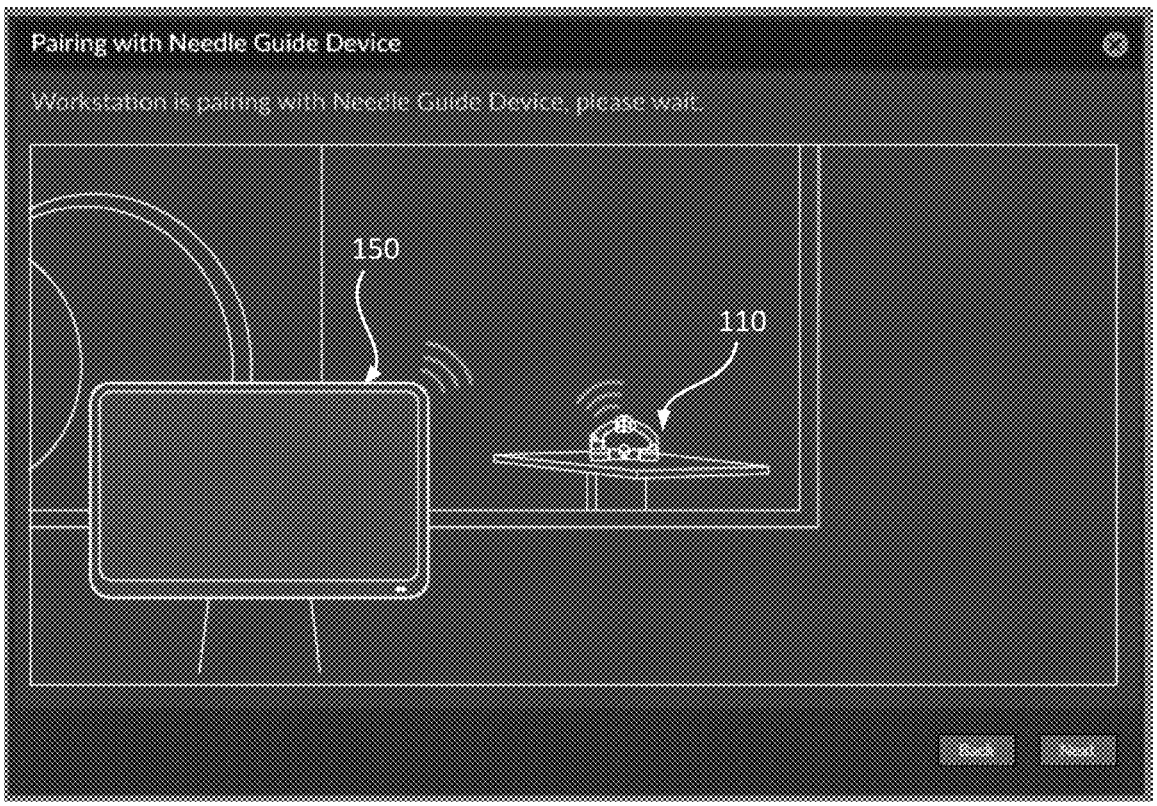
Figure 10E:
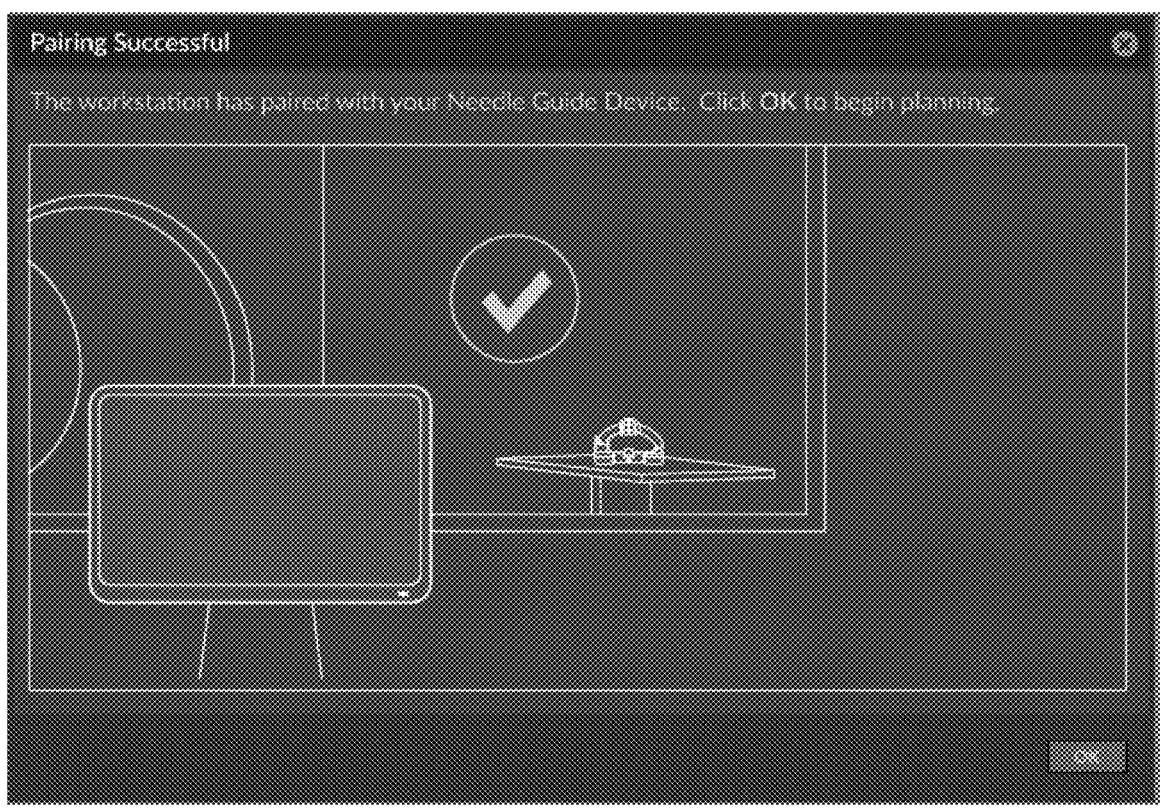

FIG. 10D and FIG. 10D illustrate the advantageous result of providing guided prompts to the user during the un-packaging and paring of the sterile and non-sterile medical devices. Specifically, as shown in FIG. 10D, the GUI 155 presents the user with a graphical guide of position and connection strength between the non-sterile device 150 and the sterile device 110. Finally, FIG. 10E shows a graphical illustration of successful positioning, pairing, and connection between the sterile device 110 and the non-sterile iso. In addition, in the event that there is a suspicion of tampering or loss of sterility, the computer or system console can be programmed to prompt the user (e.g., by issuing a warning) that the sterile medical device no should be discarded and replaced by a new one.

<FIG. 11>

Figure 11:
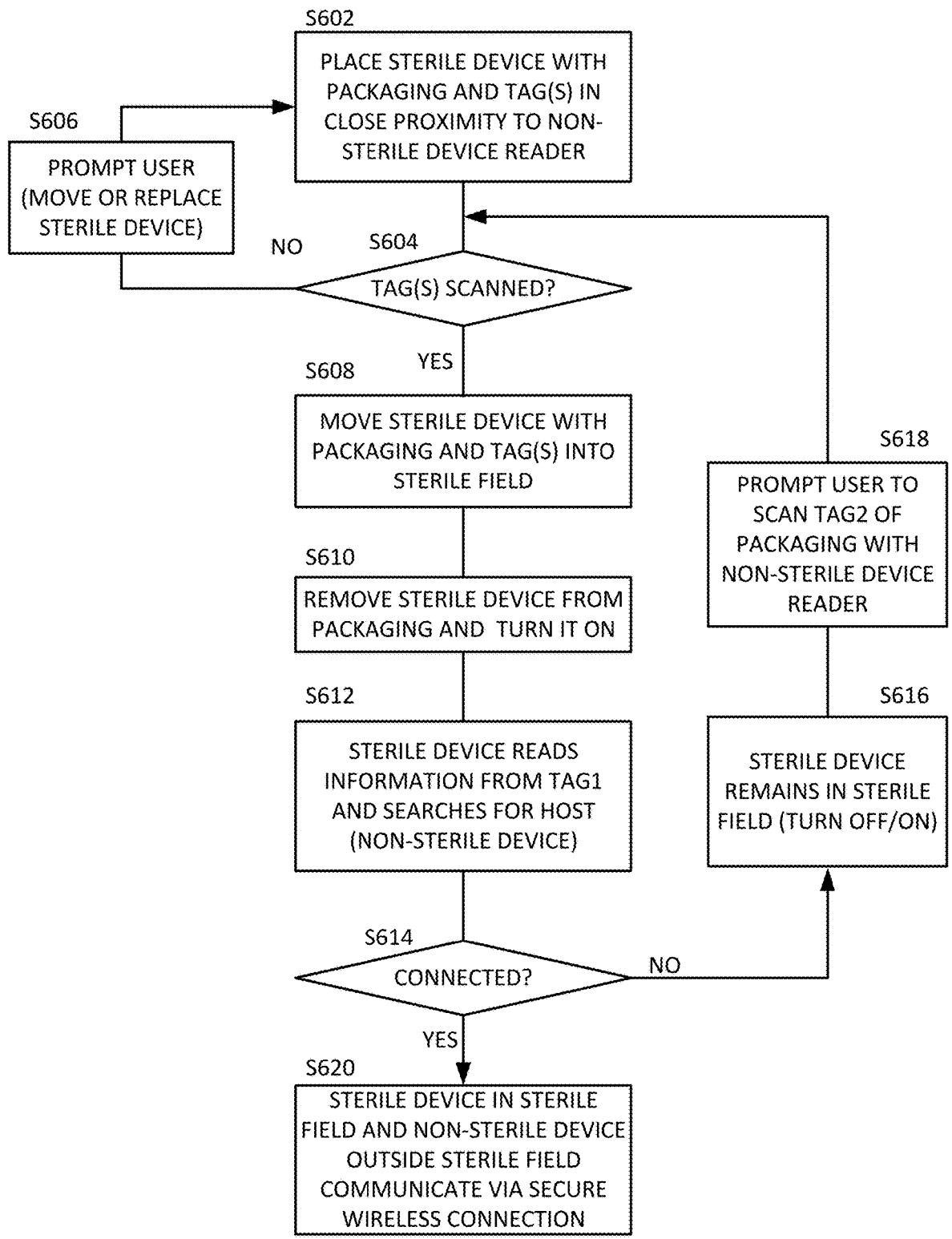
FIG. 11 illustrates a further process (method) for out-of-band pairing sterile to non-sterile devices without compromising sterility thereof.

FIG. 11 illustrates a further process (method) for out-of-band pairing sterile to non-sterile devices without compromising sterility thereof. The process of FIG. 11 is an interactive pairing process in which a user (e.g., a physician or technician) can be guided by prompts and imaging output by the GUI 155 of the non-sterile computing device 150 (shown in FIG. 9). For the process of FIG. 11, it is assumed an environment where the non-sterile computing device 150 is a console or workstation connected to a NFC reader located in a non-sterile field (e.g., a control room). The sterile device 110 is a needle guide device enclosed in a sterile packaging 120. The sterile device 110 needs to be paired with the non-sterile device 150 without compromising sterility.

According to FIG. 11, at step S602, the GUI 155 outputs an image as shown in FIG. 10A with a prompt instructing the user to place the sterile device with its packaging and NFC tag(s) in close proximity to the non-sterile device reader. At step S602, the non-sterile device 150 determines whether the tag(s) attached to the packaging or the sterile device has been properly scanned by the reader. As explained elsewhere in this disclosure, the non-sterile device 150 can either write pairing information into, or it read paring information from, at least one of the first NFC tag or the second NFC tag. In a case where at least one of the tag(s) is not properly scanned (NO at S604), the non-sterile device 150 can prompt the user to move the sterile device closer to the NFC reader, at step S606. Here, it should be recalled that the NFC tags are read using a short-range wireless communication protocol (e.g., the NFC protocol). The process of S602, S604, and S606 can be repeated a few times until at least one of the tags is scanned. If scanning of the tags fails, the processor of non-sterile device 150 can be programmed to prompt the user to replace the sterile device (i.e., to use a different/new sterile device) until at least one of the tags is properly scanned.

Once at least one of the tags is scanned (YES at S604), the process advances to step S608. Successful scanning of at least one of the tags may include reading the information stored in the second NFC tag 414 (or first NFC tag 114). Since both tags are preferably programmed with the same paring information, either of the tags can be scanned. Therefore, the use of the two tags facilitates ease and speed of scanning. At step S608, the processor of non-sterile device 150 prompts the user to carry, move, or place the sterile device 110 with its sterile packaging 120 and the corresponding NFC tags into the sterile field (e.g., the operating room). At step S610, the GUI 155 may prompt the user to open the packaging 120, remove the sterile device 110, and place the sterile components of sterile device 110 on a sterile surface (see FIG. 10B). At this time, the user may be prompted activate (turn ON) the sterile device 110, as shown in FIG. 10C. At step S612, the sterile device 110 reads pairing information from its NFC tag (TAG1) and searches for a host device (the non-sterile device), by broadcasting a connection request. Here, since the non-sterile device 150 has stored the information scanned at steps S602-S604, the processor of sterile device 150 can grant/accept the connection request received from the sterile device 110.

At step S614, the processor of non-sterile device 150 (or the communication unit 910 of the sterile device 110) can determine whether a connection between the sterile device 110 and the non-sterile device 150 has been established. If connection between the sterile device no and non-sterile device 150 is confirmed (YES at S614), the process advances to step S620. At step S620, the sterile device located in the sterile field and the non-sterile device locate outside of the sterile field are fully enabled to communicate via a secure wireless connection using a long-range wireless protocol (e.g., Bluetooth or WiFi) other than the short-range wireless protocol. Therefore, at step S620, the GUI 155 may inform the user that the sterile device 110 and non-sterile device 150 have been successfully paired to each other (see FIG. 15E)

At step S614, the processor of non-sterile device 150 could determine that a connection between the sterile device 110 and the non-sterile device 150 has not been established or cannot be established (NO at S614). There could be various reasons that may preclude establishing a connection between the sterile device no and the non-sterile device 150 even after at least one of the NFC tags has been scanned. For example, prior to starting the medical procedure, if the non-sterile device 150 or its transceiver accidently loses power or becomes disconnected, a connection could not be confirmed at step S614. Also, after powering ON, the sterile device 110 may undergo a self-test procedure. If the self-test procedure fails, it may be helpful to rescan the NFC tag of the packaging 120 with the non-sterile device 150 before discarding the sterile device 110. In either of these scenarios, the sterile device may remain in the sterile field (S616), while the user may be prompted (at step S618) to use the packaging 120 and the second NFC tag 414 to repeat the scanning step without removing the sterile device from the sterile field.

In another example a non-sterile dialysis machine needs to be paired with a sterile dialysis accessory such as a blood pressure monitor. In this example the dialysis accessory has an RFID or NFC tag embedded in the device and the sterile packaging containing the dialysis accessory has a duplicate NFC or RFID tag. Before breaking the sterile barrier either tag can be read by the non-sterile dialysis machine. After the package is opened, sterility of the dialysis accessory can be maintained by scanning only the packaging tag on the non-sterile dialysis machine.

Many medical devices require a sterilized component capable of extending into a sterile field, without risk of contaminating that field, where that sterile component interfaces with an unsterile component needed to operate the device. In this situation, the unsterile component can potentially enter the sterile field and negate the sterility of that filed. A solution to prevent loss of sterility has been to deploy a sterile barrier over any unsterile component entering the sterile field. This especially applies to medical devices used in in-vivo environments, where sterile components such as interventional robotic systems that must interface with an electronic component which cannot be sterilized.

For example a non-sterile computer needs to be paired with a sterile controller for guiding a surgical robot. The controller must maintain sterility since the doctor will use the controller with his or her sterile gloves for guiding a surgical robot. According to the present disclosure, the controller contains an embedded NFC or RFID tag and the controller in enclosed in a sterile drape or packaging. In this case too, the controller's sterile drape of packaging also contains a duplicate NFC or RFID tag. During a procedure, the doctor or technologist can scan either tag (the controller tag or the packaging tag) before the sterile packaging is opened. However, in the case that the packaging is opened before pairing, the duplicate tag in the packaging allows the physician or technologist to still pair the sterile controller with the non-sterile computer without breaking sterility of the controller.

These are only a few examples of the many possible applications in which the present disclosure can be practiced. Those skilled in the art will appreciate that there are many other aspects under which the present disclosure may be practiced.

According to a first aspect (aspect 1) the present disclosure can be practiced as a system for out-of-band pairing sterile and non-sterile devices without compromising sterility thereof, the system comprising: a sterile medical device; a non-sterile device; a sterile packaging enclosing at least the sterile medical device; at least one NFC tag configured to store identifying information of the sterile medical device; a NFC transceiver configured to communicate with the NFC tag via a first wireless protocol; and a processor and a memory coupled to the processor, the memory storing instructions executable by the processor to: receive a pairing request signal from the sterile medical device located inside a sterile field; transmit the pairing request signal to the non-sterile device located outside the sterile field; and wherein, in response to receiving the paring request signal, the processor configures the sterile medical device to use the identifying information stored in the at least one NFC tag to wirelessly connect with the non-sterile device via a second wireless protocol which is different from the first wireless protocol.

According to a second aspect (aspect 2) the present disclosure can be practiced as the system of aspect 1, wherein the non-sterile device includes the NFC transceiver, wherein the NFC transceiver is configured to write the identifying information into the at least one NFC tag, and wherein the sterile medical device includes a NFC reader configured to read the identifying information from the at least one NFC tag.

According to a third aspect (aspect 3) the present disclosure can be practiced as the system of aspect 1, wherein the at least one NFC tag is integrated into the sterile medical device, and wherein the identifying information includes a wireless identifier and/or encryption key which serves to associate the sterile medical device with the non-sterile device.

According to a fourth aspect (aspect 4) the present disclosure can be practiced as the system of aspect 1, wherein the at least one NFC tag includes an RFID tag integrated into the sterile medical device.

According to a fifth aspect (aspect 5) the present disclosure can be practiced as the system of aspect 1, wherein the at least one NFC tag includes a first NFC tag integrated into the sterile medical device and a second NFC tag integrated into the sterile packaging.

According to a sixth aspect (aspect 6) the present disclosure can be practiced as the system of aspect 5, wherein the non-sterile device is configured to write the identifying information into both the first NFC tag and the second NFC tag, and the sterile medical device is configured to read the identifying information from the first NFC tag, and wherein the non-sterile device and the sterile medical device use the identifying information read from the first NFC tag to wirelessly connect with each other, in response to receiving the paring request signal.

According to a seventh aspect (aspect 7) the present disclosure can be practiced as the system of aspect 6, wherein the sterile medical device includes one or more of a needle guidance device, a sterile dialysis machine, and a sterile controller for guiding a surgical robot.

According to an eighth aspect (aspect 8) the present disclosure can be practiced as the system of aspect 1, wherein the at least one NFC tag includes an antenna, an integrated circuit, and a memory which stores a password protected wireless encryption key, wherein the non-sterile device includes a NFC transceiver configured to transmit an unlocking password to the at least one NFC tag, and wherein, in response to receiving the unlock password, the at least one NFC tag transmits the wireless encryption key to the non-sterile device.

According to a ninth aspect (aspect 9) the present disclosure can be practiced as the system of aspect 5, further comprising: a manufacturer programming unit configured to program the first and second NFC tags with an encryption key after the sterile medical device has been enclosed with the sterile packaging, thus eliminating risk of key mismatch between the first NFC tag and the second NFC tag.

According to a ninth(b) aspect (aspect 9b) the present disclosure can be practiced as the system of aspect 3, further comprising: a manufacturer programming unit configured to program the at least one NFC tag integrated in the sterile medical device with an encryption key after the sterile medical device has been enclosed with the sterile packaging, wherein the encryption key serves to associate the sterile medical device with the non-sterile device thus eliminating risk of key mismatch between the sterile medical device and non-sterile device. According to this aspect (aspect 9b), when the sterilization process would include a risk to damage or breaking some sensitive parts of the sterile device, or a risk to fail sterilization, it would be advantageous if we can complete a definition process of the encryption key after the sterilization process. This would reduce risk to do unnecessary manufacturing steps, and would ensure proper sterilization and paring security.

According to a tenth aspect (aspect 10), the present disclosure can be practiced as the system of aspect 5, wherein both the first NFC tag and the second NFC tag are configured with identical identification information, wherein, before opening of the sterile packaging, either the first NFC tag or the second NFC tag is scanned with a scanner of the non-sterile device to initiate wireless pairing, and wherein, after opening of the sterile packaging, only the second NFC tag integrated with the sterile packaging is scanned with the scanner to initiate wireless pairing.

According to an eleventh aspect (aspect 11), the present disclosure can be practiced as a method for out-of-band pairing sterile and non-sterile devices without compromising sterility thereof, the method comprising: forming a communication system comprising: a sterile medical device integrated with a first near field communication (NFC) tag; a non-sterile device; and a sterile packaging integrated with a second NFC tag and enclosing the sterile medical device and the first NFC tag, storing identical identification information in the first NFC tag and in the second NFC tag; and scanning the first NFC tag or the second NFC tag with the non-sterile device according to a status of the sterile packaging, wherein, before opening of the sterile packaging, either the first NFC tag or the second NFC tag is scanned with the non-sterile device to initiate wireless pairing, and wherein, after opening of the sterile packaging, only the second NFC tag integrated in the sterile packaging is scanned with the non-sterile device to initiate wireless pairing.

According to a twelfth aspect (aspect 12), the present disclosure can be practiced as the method of aspect 11, further comprising: writing the identical identifying information into both the first NFC tag and the second NFC tag before the opening of the sterile packaging.

According to a thirteenth aspect (aspect 13), the present disclosure can be practiced as the method of aspect 11, further comprising: after opening of the sterile packaging, transmitting the identification information from the second NFC tag to the non-sterile device to initiate the wireless paring.

According to a fourteenth aspect (aspect 14), the present disclosure can be practiced as the method of aspect 11, wherein the identifying information includes a wireless identifier and an encryption key which serves to enable wireless communication between the sterile medical device and the non-sterile device.

According to a fifteenth aspect (aspect 15), the present disclosure can be practiced as the method of aspect 11, wherein the non-sterile device is configured to write the identifying information into both the first NFC tag and the second NFC tag, and the sterile medical device is configured to read the identifying information from the first NFC tag, and wherein the non-sterile device and the sterile medical device use the identifying information read from the first NFC tag to wirelessly connect with each other, in response to a received paring request signal.

According to a sixteenth aspect (aspect 16), the present disclosure can be practiced as the method of aspect 11, wherein the sterile medical device includes one or more of a needle guidance device, a sterile dialysis machine, and a sterile controller for guiding a surgical robot, and wherein the pairing includes pairing at least one of the needle guidance device, the sterile dialysis machine, and the sterile controller for guiding a surgical robot with the non-sterile medical device for secure wireless communication.

According to a seventeenth aspect (aspect 17), the present disclosure can be practiced as the method of aspect 11, wherein the first NFC tag and the second NFC tag are configured with a password protected wireless encryption key, wherein the non-sterile device includes a NFC transceiver configured to transmit an unlocking password to at least one of the first and second NFC tag, and wherein, in response to receiving the unlock password, the at least one of the first and second NFC tag transmits the encryption key to the non-sterile device.

According to an eighteenth aspect (aspect 18), the present disclosure can be practiced as the method of aspect 11, further comprising: programming the first and second NFC tags with an encryption key after the sterile medical device has been enclosed with the sterile packaging, thus eliminating risk of key mismatch between the first NFC tag and the second NFC tag.

According to a nineteenth aspect (aspect 19), the present disclosure can be practiced as the method of aspect 11, wherein both the first NFC tag and the second NFC tag are configured with identical identification information, wherein, before opening of the sterile packaging, either the first NFC tag or the second NFC tag is scanned with the non-sterile device to initiate wireless pairing, and wherein, after opening of the sterile packaging, only the second NFC tag integrated in the sterile package is scanned with the non-sterile device to initiate wireless pairing.

According to a twentieth aspect (aspect 20), the present disclosure can be practiced as a method for out-of-band pairing sterile and non-sterile devices without compromising sterility thereof, the method comprising the steps of: (a) forming a communication system comprising: a sterile medical device, a non-sterile device, a sterile packaging enclosing at least the sterile medical device, at least one NFC tag integrated with the sterile medical device and storing identifying information about the sterile medical device, and a NFC transceiver operatively connected to the non-sterile device and configured to communicate with the at least one NFC tag via a first wireless protocol; (b) during a pairing process, scanning the at least NFC tag with the NFC transceiver and exchanging paring information via the first wireless protocol; and (c) during a medical procedure: (c1) activating the at least one NFC tag, and (c2) transmitting a connection request from the sterile medical device located inside a sterile field to the non-sterile device located outside the sterile field, wherein the sterile medical device uses the paring information and the identifying information stored in the at least one NFC tag to wirelessly connect with the non-sterile device via a second wireless protocol which is different from the first wireless protocol.

According to a twenty first aspect (aspect 21) the present disclosure can be practiced as the method of aspect 20, wherein, during the pairing process, the step of exchanging paring information via the first wireless protocol includes programming the at least one NFC tag integrated in the sterile medical device with an encryption key after the sterile medical device has been enclosed with the sterile packaging, wherein the encryption key serves to associate the sterile medical device with the non-sterile device thus eliminating risk of key mismatch between the sterile medical device and non-sterile device.

According to a twenty second aspect (aspect 22), the present disclosure can be practiced as a system for out-of-band pairing sterile and non-sterile medical devices without compromising sterility thereof, the system comprising: a sterile medical device; a non-sterile device; at least one near field communication (NFC) tag configured to store information about of the sterile medical device; and a processor coupled to a memory which stores instructions executable by the processor to: prompt a user to place the at least one NFC tag within close proximity of the non-sterile device, establish a first wireless connection between the non-sterile medical device and the at least one NFC tag for transmitting the information about of the sterile medical device from the NFC tag to the non-sterile medical device, and establish a second wireless connection between the sterile medical device located inside a sterile filed and the non-sterile device located outside the sterile field for exchanging operational information between the sterile medical device and the non-sterile device, wherein the processor establishes the second wireless connection based on the information about the sterile medical device read from the NFC tag, and wherein the processor establishes the first wireless connection for transmitting the paring information between the at least NFC tag and the non-sterile medical device over a NFC protocol, and establishes the second wireless connection for exchanging operational information between the sterile medical device and the non-sterile device over a short or long range wireless communication protocol different from the NFC protocol.

In describing the exemplary embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Therefore, while the present disclosure has been described with reference to exemplary embodiments, it is to be understood that the present disclosure is not limited to the disclosed exemplary embodiments. The scope of the following claims is to be accorded the broadest reasonable interpretation so as to encompass all such modifications and equivalent structures and functions.

What is claimed is:

1. A system for controlling out-of-band pairing of sterile and non-sterile devices without compromising sterility thereof, the system comprising:
    a non-sterile device;
    a sterile medical device;
    a sterile packaging enclosing the sterile medical device; and
    an electronic circuit configured to store pairing information and coupled to one or more of the sterile packaging and the sterile medical device,
    wherein the non-sterile device is configured to scan the electronic circuit to exchange pairing information about the sterile medical device via a short-range wireless protocol, wherein the sterile medical device is configured read the pairing information from the electronic circuit and transmit a request for wireless connection to the non-sterile device,
and
wherein, in response to receiving the request for wireless connection, the non-sterile device located outside a sterile field establishes a secure wireless connection with the sterile medical device located in the sterile field via a long-range wireless protocol using the paring information stored in the electronic circuit.

2. The system according to claim 1,
wherein the non-sterile device exchanges the pairing information before the sterile packaging is opened and while the sterile medical device is in a deactivated state, and
wherein the sterile medical device transmits the request for wireless connection to the non-sterile device after the sterile medical device is removed from the sterile packaging and is placed in an active state.

3. The system according to claim 1,
wherein the electronic circuit includes a first near field communication (NFC) tag coupled to the sterile medical device, and a second NFC tag coupled to the sterile packaging,
wherein the non-sterile device includes a NFC transceiver configured to transmit and store the pairing information in the first NFC tag and the second NFC tag via the short-range wireless protocol, and
wherein the sterile medical device is configured to read the pairing information from the first NFC tag coupled thereto, and transmit the pairing information read from the first NFC tag to the non-sterile device to establish the secure wireless communication between the sterile medical device located in the sterile field and the non-sterile device located outside the sterile field.

4. The system according to claim 1,
wherein the electronic circuit includes a first near field communication (NFC) tag coupled to the sterile medical device, and a second NFC tag coupled to the sterile packaging,
wherein the non-sterile device includes a NFC transceiver configured to read the pairing information from at least one of the first NFC tag and second NFC tag via the short-range wireless protocol, and store the pairing information in a memory of the non-sterile device, and
wherein the sterile medical device is configured to read the pairing information from the first NFC tag coupled thereto, and transmit the pairing information read from the first NFC tag to the non-sterile device to establish the secure wireless connection between the sterile medical device located in the sterile field and the non-sterile device located outside the sterile field.

5. The system according to claim 1,
wherein the pairing information includes one or more of a wireless identifier, an encryption key, and a password which serves to associate the sterile medical device with the non-sterile device for secure communication with each other.

6. The system according to claim 1,
wherein the electronic circuit includes a first near field communication (NFC) tag coupled to the sterile medical device, and a second NFC tag coupled to the sterile packaging, and wherein the first NFC tag includes a passive RFID tag coupled to the sterile medical device, and the second NFC tag includes a passive RFID tag integrated into the sterile packaging.

7. The system according to claim 1, further comprising:
a processor and a memory coupled to one or more of the non-sterile device and the sterile medical device, the memory storing instructions executable by the processor to:
prompt a user to place the sterile medical device enclosed in the sterile packaging in the non-sterile field, and scan the electronic circuit with the non-sterile device.

8. The system according to claim 7,
wherein the electronic circuit includes a first near field communication (NFC) tag coupled to the sterile medical device, and a second NFC tag coupled to the sterile packaging,
wherein the processor is further configured to:
determine if at least one of the first NFC tag or the second NFC tag has been scanned by a NFC transceiver of the non-sterile device, and
prompt the user to place the sterile medical device enclosed in the sterile packaging in the sterile field, remove the sterile medical device from the sterile packaging, and turn ON the sterile medical device to establish the secure wireless connection.

9. The system according to claim 1,
wherein the sterile medical device includes one or more of a needle guidance device, a sterile dialysis machine, and a sterile controller for guiding a surgical robot.

10. The system according to claim 1,
wherein the electronic circuit includes a first near field communication (NFC) tag coupled to the sterile medical device, and a second NFC tag coupled to the sterile packaging,
wherein the first and second NFC tags each includes an antenna, an integrated circuit, and a memory storing a wireless encryption key with is password-protected,
wherein the non-sterile device includes a NFC transceiver configured to transmit an unlocking password to at least one of the first and second NFC tags, and
wherein, in response to receiving the unlocking password, the at least one of the first and second NFC tags transmits the wireless encryption key to the non-sterile device.

11. The system according to claim 10, further comprising:
a programming unit configured to program one or more of the first and second NFC tags with an encryption key after the sterile packaging has been coupled to the second NFC tag, and after the sterile medical device coupled to the first NFC tag have been enclosed with the sterile packaging.

12. The system according to claim 10,
wherein both the first NFC tag and the second NFC tag are configured with identical pairing information,
wherein, before opening of the sterile packaging, either the first NFC tag or the second NFC tag is scanned with a scanner of the non-sterile device to initiate wireless pairing, and
wherein, after opening of the sterile packaging, only the second NFC tag integrated with the sterile packaging is scanned with the scanner to initiate wireless pairing.

13. A method for controlling out-of-band pairing in a system of sterile and non-sterile devices without compromising sterility thereof, the system comprising a non-sterile device, a sterile medical device, a sterile packaging enclosing the sterile medical device, and an electronic circuit configured to store pairing information and coupled to one or more of the sterile packaging and the sterile medical device, the method comprising:

scanning the electronic circuit with the non-sterile device to exchange pairing information about the sterile medical device via a short-range wireless protocol, reading the pairing information from the electronic circuit with the sterile medical device, and transmitting, by the sterile medical device, a request for wireless connection to the non-sterile device, wherein, in response to receiving the request for wireless connection, the non-sterile device located outside a sterile field establishes a secure wireless connection with the sterile medical device located in the sterile field via a long-range wireless protocol using the pairing information stored in the electronic circuit.

14. A method for controlling out-of-band pairing in a system of sterile and non-sterile devices without compromising sterility thereof, the system comprising: a non-sterile device, a sterile medical device coupled to a first near field communication (NFC) tag, a packaging coupled to a second NFC tag and enclosing the sterile medical device, the method comprising:

exchanging pairing information between the non-sterile device and the first and/or second NFC tags via a short-range wireless protocol;

storing the pairing information in the first NFC tag and in the second NFC tag;

exchanging a request for wireless connection between the sterile medical device located in a sterile field and the non-sterile device located outside the sterile field via a long-range wireless protocol different from the short-range wireless protocol; and establishing secure wireless communication between the sterile medical device located in the sterile field and the non-sterile device located outside the sterile field via the long-range wireless protocol using the pairing information stored in the second NFC tag.

15. The method according to claim 14, wherein the non-sterile device exchanges the pairing information before the sterile packaging is opened and while the sterile medical device is in a deactivated state, and wherein the sterile medical device transmits the request for wireless connection to the non-sterile device after the sterile medical device is removed from the sterile packaging and is placed in an active state.

16. The method according to claim 15, wherein exchanging pairing information includes, by the non-sterile device, transmitting and storing the pairing information in the first NFC tag and the second NFC tag via the short-range wireless protocol, and wherein, in establishing a secure wireless connection, the sterile medical device reads the pairing information from the first NFC tag coupled thereto, and transmits the pairing information read from the first NFC tag to the non-sterile device to establish the secure wireless communication between the sterile medical device located in the sterile field and the non-sterile device located outside the sterile field.

17. The method according to claim 15, wherein exchanging pairing information includes, by the non-sterile device, reading the pairing information from at least one of the first NFC tag and second NFC tag via the short-range wireless protocol, and storing the pairing information in a memory of the non-sterile device, and wherein, in establishing a secure wireless connection, the sterile medical device reads the pairing information from the first NFC tag coupled thereto, and transmits the pairing information read from the first NFC tag to the non-sterile device to establish the secure wireless connection between the sterile medical device located in the sterile field and the non-sterile device located outside the sterile field.

18. The method according to claim 15, further comprising:

programming one or more of the first and second NFC tags with an encryption key after the sterile packaging has been coupled to the second NFC tag, and after the sterile medical device coupled to the first NFC tag have been enclosed with the sterile packaging.

19. The method according to claim 14, further comprising:

prompting a user, by a processor coupled to one or more of the non-sterile device and the sterile medical device, to place the sterile medical device enclosed in the sterile packaging in the non-sterile field, and scanning the first NFC tag and/or the second NFC tag with a NFC transceiver of the non-sterile device.

20. The method according to claim 19, further comprising:

determining, by the processor, if at least one of the first NFC tag or the second NFC tag has been scanned by the NFC transceiver of the non-sterile device, and prompting the user, by the processor, to place the sterile medical device enclosed in the sterile packaging in the sterile field, remove the sterile medical device from the sterile packaging, and turn ON the sterile medical device to establish the secure wireless connection.

\* \* \* \* \*